United States Patent [19]

Patchett et al.

[11] Patent Number: 5,124,335

[45] Date of Patent: Jun. 23, 1992

[54] SUBSTITUTED PYROLLO-FUSED 6 MEMBERED HETEROCYCLES AS ANGIOTENSIN II ANTAGONISTS

[75] Inventors: Arthur A. Patchett; Nathan B. Mantlo, both of Westfield; William J. Greenlee, Teaneck, all of N.J.

[73] Assignee: Merck & Co., Inc., Rahway, N.J.

[21] Appl. No.: 647,876

[22] Filed: Jan. 30, 1991

[51] Int. Cl.$^5$ .................... A61K 31/435; C07D 471/04
[52] U.S. Cl. ...................... 514/300; 546/23; 546/113; 544/127; 514/81
[58] Field of Search ............. 546/113, 23; 544/127; 514/81, 300

[56] References Cited

FOREIGN PATENT DOCUMENTS 399731 11/1920 European Pat. Off. .
400974 12/1990 European Pat. Off. .

*Primary Examiner*—Bernard Dentz
*Attorney, Agent, or Firm*—William H. Nicholson; Joseph F. Diprima

[57] ABSTRACT

Substituted pyrrolo-fused 6-membered heterocycles of structural formula:

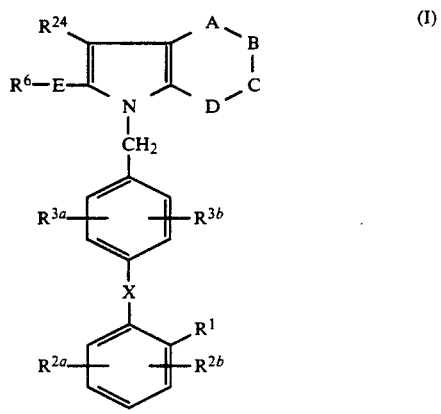

wherein A, B, C, and D are independently carbon atoms or nitrogen atoms are angiotensin II antagonists useful in the treatment of hypertension and congestive heart failure.

12 Claims, No Drawings

SUBSTITUTED PYROLLO-FUSED 6 MEMBERED HETEROCYCLES AS ANGIOTENSIN II ANTAGONISTS

SUMMARY OF THE INVENTION

This invention relates to novel compounds of structural formula I which are angiotensin II antagonists useful in the treatment of hypertension, congestive heart failure, and elevated intraocular pressure.

It also relates to processes for preparing the novel compounds; pharmaceutical formulations comprising one or more of the compounds as active ingredient; and a method of treatment of hypertension, congestive heart failure, and elevated intraocular pressure.

The compounds of this invention also exhibit central nervous system (CNS) activity. They are useful in the treatment of cognitive dysfunctions including Alzheimer's disease, amnesia and senile dementia. These compounds also have anxiolytic and antidepressant properties and are therefore, useful in the relief of symptoms of anxiety and tension and in the treatment of patients with depressed or dysphoric mental states.

Further, these compounds exhibit antidopaminergic properties and are thus useful to treat disorders that involve dopamine dysfunction such as schizophrenia. The compounds of this invention are especially useful in the treatment of these conditions in patients who are also hypertensive or have a congestive heart failure condition.

BACKGROUND OF THE INVENTION

Renin-angiotensin system (RAS) plays a central role in the regulation of normal blood pressure and seems to be critically involved in hypertension development and maintenance as well as congestive heart failure. Angiotensin II (AII), an octapeptide hormone is produced mainly in the blood during the cleavage of angiotensin I by angiotensin converting enzyme (ACE) localized on the endothelium of blood vessels of lung, kidney, and many other organs, and is the end product of the RAS. AII is a powerful arterial vasoconstricter that exerts its action by interacting with specific receptors present on cell membranes. One of the possible modes of controlling the RAS is angiotensin II receptor antagonism. Several peptide analogs of A II are known to inhibit the effect of this hormone by competitively blocking the receptors, but their experimental and clinical applications have been limited by the partial agonist activity and lack of oral absorption [M. Antonaccio. *Clin. Exp. Hypertens.* A4, 27-46 (1982); D. H. P. Streeten and G. H. Anderson, Jr.—*Handbook of Hypertension, Clinical Pharmacology of Antihypertensive Drugs,* ed. A. E. Doyle, Vol. 5, pp. 246-271, Elsevier Science Publisher, Amsterdam, The Netherlands, 1984].

Recently, several non-peptide compounds have been described as A II antagonists. Illustrative of such compounds are those disclosed in U.S. Pat. Nos. 4,207,324; 4,340,598; 4,576,958; 4,582,847; and 4,880,804; in European Patent Applications 028,834; 245,637; 253,310; 399,731; 400,974; and 291,969; and in articles by A. T. Chiu, et al. [*Eur. J. Pharm. Exp. Therap,* 157, 13-21 (1988)] and by P. C. Wong, et al. [*J. Pharm. Exp. Therap,* 247, 1-7 (1988)]. All of the U.S. Patents, European Patent Applications 028,834 and 253,310 and the two articles disclose substituted imidazole compounds which are generally bonded through a lower alkyl bridge to a substituted phenyl. European Patent Application 245,637 discloses derivatives of 4,5,6,7-tetrahydro-2H-imidazo[4,5-c]-pyridine-6-carboxylic acid and analogs thereof as antihypertensive agents.

None of the compounds disclosed in the above identified U.S. Patents, European Applications and articles have the heterobicyclic structure of the compounds of this invention.

DETAILED DESCRIPTION OF THE INVENTION

This invention relates to substituted pyrrolo-fused 6-membered ring heterocycles of the formula I shown below which are angiotensin II antagonists and are useful in the treatment of hypertension, congestive heart failure, and elevated intraocular pressure.

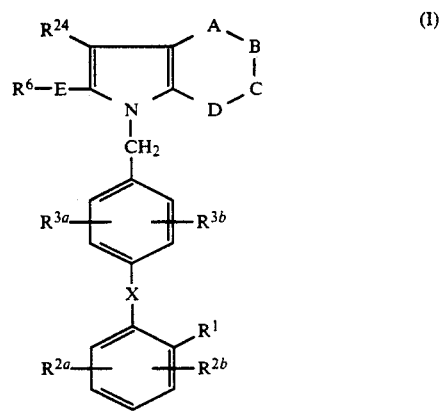

wherein:
$R^1$ is
(a) $-CO_2R^4$,
(b) $-SO_3R^5$,
(c) $-NHSO_2CF_3$,
(d) $-PO(OR^5)_2$,
(e) $-SO_2-NH-R^9$,
(f) $-CONHOR^5$,

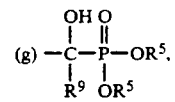

(h) $-SO_2NH$-heteroaryl,
(i) $-CH_2SO_2NH$-heteroaryl,
(j) $-SO_2NHCO-R^{23}$,
(k) $-CH_2SO_2NHCO-R^{23}$,
(l) $-CONH-SO_2R^{23}$,
(m) $-CH_2CONH-SO_2R^{23}$,
(n) $-NHSO_2NHCO-R^{23}$,
(o) $-NHCONHSO_2-R^{23}$,
(p) $-SO_2NHCONR^{23}$,

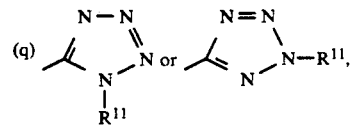

-continued (r) 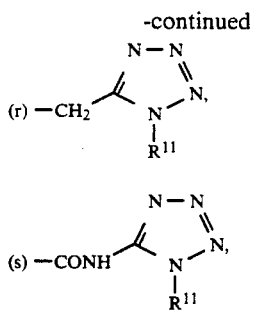

(t) —CONHNHSO$_2$CF$_3$,

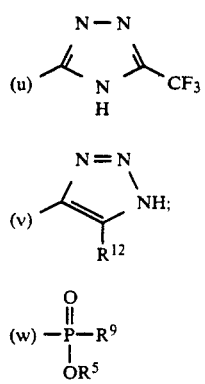

(w) 
$$-\overset{O}{\underset{OR^5}{\overset{\|}{P}}}-R^9$$

wherein heteroaryl is an unsubstituted, monosubstituted or disubstituted five- or six-membered aromatic ring which contains 1 to 3 heteroatoms selected from the group consisting of O, N or S and wherein the substituents are members selected from the group consisting of —OH, —SH, —C$_1$-C$_4$-alkyl, —C$_1$-C$_4$-alkoxy, Cl, Br, F, I, —NO$_2$, —CO$_2$H, —CO$_2$—C$_1$-C$_4$-alkyl, —NH$_2$, —NH(-C$_1$-C$_4$-alkyl) and —N(C$_1$-C$_4$-alkyl)$_2$;

R$^{2a}$ and R$^{2b}$ are independently H, Cl, Br, I, F, —NO$_2$, —NH$_2$, C$_1$-C$_4$-alkylamino, di(C$_1$-C$_4$ alkyl)amino, —SO$_2$NHR$^9$, CF$_3$, C$_1$-C$_4$-alkyl, or C$_1$-C$_4$-alkoxy;

R$^{3a}$ is
(a) H,
(b) Cl, Br, I, or F,
(c) C$_1$-C$_6$-alkyl,
(d) C$_1$-C$_6$-alkoxy,
(e) C$_1$-C$_6$-alkoxyalkyl;

R$^{3b}$ is
(a) H,
(b) Cl, Br, I, or F,
(c) NO$_2$,
(d) C$_1$-C$_6$-alkyl,
(e) C$_1$-C$_6$-acyloxy,
(f) C$_1$-C$_6$-cycloalkyl,
(g) C$_1$-C$_6$-alkoxy,
(h) —NHSO$_2$R$^4$,
(i) hydroxy C$_1$-C$_4$-alkyl,
(j) aryl C$_1$-C$_4$-alkyl,
(k) C$_1$-C$_4$-alkylthio,
(l) C$_1$-C$_4$-alkyl sulfinyl,
(m) C$_1$-C$_4$-alkyl sulfonyl,
(n) NH$_2$,
(o) C$_1$-C$_4$-alkylamino,
(p) C$_1$-C$_4$-dialkylamino,
(q) fluoro C$_1$-C$_4$-alkyl,
(r) —SO$_2$—NHR$^9$,
(s) aryl, or
(t) furyl;

wherein aryl is phenyl or naphthyl or substituted phenyl or naphthyl with one or two substituents selected from the group consisting of Cl, Br, I, F, C$_1$-C$_4$-alkyl, C$_1$-C$_4$-alkoxy, NO$_2$, CF$_3$, C$_1$-C$_4$-alkylthio, OH, NH$_2$, NH(C$_1$-C$_4$-alkyl), N(C$_1$-C$_4$-alkyl)$_2$, CO$_2$H, and CO$_2$—C$_1$-C$_4$-alkyl;

R$^4$ is H, C$_1$-C$_6$ alkyl, aryl or —CH$_2$-aryl;
R$^{4a}$ is C$_1$-C$_6$-alkyl, aryl or —CH$_2$-aryl;
R$^5$ is

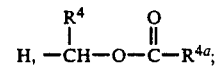

E is a single bond, —NR$^{13}$(CH$_2$)$_s$—, —S(O)$_x$—(CH$_2$)$_s$— where x is 0 to 2 and s is 0 to 5, —CH(OH)—, —O—, —CO—;

R$^6$ is
(a) aryl or substituted aryl with 1 or 2 substituents selected from the group consisting of Cl, Br, I, F —O—C$_1$-C$_4$-alkyl, C$_1$-C$_4$-alkyl, —NO$_2$, —CF$_3$, —SO$_2$NR$^9$R$^{10}$, —S—C$_1$-C$_4$-alkyl, —OH, —NH$_2$, C$_3$-C$_7$-cycloalkyl, C$_3$-C$_{10}$-alkenyl;
(b) C$_1$-C$_9$-alkyl, C$_2$-C$_6$-alkenyl or C$_2$-C$_6$-alkynyl or substituted C$_1$-C$_9$ alkyl, C$_2$-C$_6$ alkenyl or C$_2$-C$_6$ alkynyl with a substituent selected from the group consisting of aryl, C$_3$-C$_7$-cycloalkyl, Cl, Br, I, F, —OH, —NH$_2$, —NH(C$_1$-C$_4$-alkyl), —CF$_2$CF$_3$, —N(C$_1$-C$_4$-alkyl)$_2$, —NH—SO$_2$R$^4$, —COOR$^4$, —CF$_3$, —CF$_2$CH$_3$, —SO$_2$NHR$^9$; or
(c) an unsubstituted, monosubstituted or disubstituted aromatic 5 or 6 membered cyclic ring which contains one or two members selected from the group consisting of N, O, S, and wherein the substituents are members selected from the group consisting of —OH, —SH, C$_1$-C$_4$-alkyl, C$_1$-C$_4$-alkyloxy, —CF$_3$, Cl, Br, I, F, or NO$_2$,
(d) perfluoro—C$_1$-C$_4$-alkyl,
(e) C$_3$-C$_7$-cycloalkyl or mono- or disubstituted with C$_1$-C$_4$-alkyl or —CF$_3$;

R$^9$ is H, C$_1$-C$_5$-alkyl, aryl or —CH$_2$-aryl;
R$^{10}$ is H, C$_1$-C$_4$-alkyl;
R$^{11}$ is H, C$_1$-C$_6$-alkyl, C$_2$-C$_4$-alkenyl, C$_1$-C$_4$-alkoxy—C$_1$-C$_4$-alkyl, or

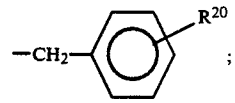

R$^{12}$ is —CN, —NO$_2$ or —CO$_2$R$^4$;
R$^{13}$ is H, —CO(C$_1$-C$_4$-alkyl), C$_1$-C$_6$-alkyl, allyl, C$_3$-C$_6$-cycloalkyl, phenyl or benzyl;
R$^{14}$ is H, C$_1$-C$_8$-alkyl, C$_1$-C$_8$-perfluoroalkyl, C$_3$-C$_6$-cycloalkyl, phenyl or benzyl;
R$^{15}$ is H, C$_1$-C$_6$-alkyl;
R$^{16}$ is H, C$_1$-C$_6$-alkyl, C$_3$-C$_6$-cycloalkyl, phenyl or benzyl;
R$^{17}$ is —NR$^9$R$^{10}$, —OR$^{10}$, —NHCONH$_2$, —NHCSNH$_2$,

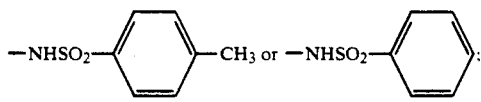

$R^{18}$ and $R^{19}$ are independently $C_1$-$C_4$-alkyl or taken together are —$(CH_2)_q$— where $q$ is 2 or 3;

$R^{20}$ is H, —$NO_2$, —$NH_2$, —OH or —$OCH_3$;

$R^{23}$ is
(a) aryl,
(b) heteroaryl,
(c) $C_3$-$C_4$-cycloalkyl,
(d) $C_1$-$C_4$-alkyl or substituted $C_1$-$C_4$ alkyl with a substituent that is a member selected from the group consisting of aryl, heteroaryl, —OH, —SH, —$C_1$-$C_4$-alkyl, —$O(C_1$-$C_4$-alkyl), —S(-$C_1$-$C_4$-alkyl), —$CF_3$, Cl, Br, F, I, —$NO_2$, —$CO_2H$, —$CO_2$—$C_1$-$C_4$-alkyl, —$NH_2$, —NH(-$C_1$-$C_4$-alkyl), —$NHCOR^{4a}$, —$N(C_1$-$C_4$-alkyl$)_2$, —$PO_3H$, —PO(OH)($C_1$-$C_4$-alkyl), —PO(OH)-(aryl), or —PO(OH)(O—$C_1$-$C_4$-alkyl),
(e) perfluoro-$C_1$-$C_4$-alkyl;

$R^{24}$ is
(a) hydrogen,
(b) $C_1$-$C_6$ alkyl or substituted $C_1$-$C_6$ alkyl with a substituent selected from
  (i) $C_1$-$C_4$ alkyloxy,
  (ii) aryl,
  (iii) —$N(R^4)_2$,
  (iv) —OH,
  (v) —$CO_2R^4$,
  (vi) —$CF_3$,
  (vii) —$CON(R^4)_2$, or
  (viii) $C_3$-$C_7$ cycloalkyl,
(c) $C_3$-$C_7$ cycloalkyl or substituted $C_3$-$C_7$ cycloalkyl with a substituent selected from
  (i) $C_1$-$C_4$ alkyl,
  (ii) $C_1$-$C_4$ alkoxy,
  (iii) aryl,
  (iv) —$N(R^4)_2$,
  (v) —OH,
  (vi) —$CO_2R^4$,
  (vii) —$CF_3$, or
  (viii) —$CON(R^4)_2$,
(d) aryl,
(e) —$C_1$-$C_4$ alkoxy,
(f) —$C_1$-$C_4$ acyloxy,
(g) —$N(R^8)CO_2R^{4a}$,
(h) —CN,
(i) —$OC(O)OR^{4a}$,
(j) —$OC(O)N(R^4)_2$,
(k) —$N(R^8)CON(R^4)_2$,
(l) —$CF_3$, —$CF_2CF_3$ or —$CF_2CH_3$,
(m) —OH or —SH, or
(n) —$CO_2R^4$;

X is
(a) a carbon-carbon single bond,
(b) —CO—,
(c) —O—,
(d) —S—,
(e) —N—,
   |
   $R^{13}$ -continued (f) —CON—,
   |
   $R^{15}$ (g) —NCO—,
   |
   $R^{15}$ (h) —$OCH_2$—,
(i) —$CH_2O$—
(j) —$SCH_2$—,
(k) —$CH_2S$—,
(l) —$NHC(R^9)(R^{10})$,
(m) —$NR^9SO_2$—,
(n) —$SO_2NR^9$—,
(o) —$C(R^9)(R^{10})NH$—,
(p) —CH=CH—,
(q) —CF=CF—,
(r) —CH=CF—,
(s) —CF=CH—,
(t) —$CH_2CH_2$—,
(u) —$CF_2CF_2$—, (v) —CH——CH— and 
          \  /
           $CH_2$ $CH_2$
       /    \
      C
       \    /
        $CH_2$ $OR^{14}$
      |
(w) —CH—, $OCOR^{16}$
      |
(x) —CH—

$NR^{17}$
      ||
(y) —C— , or $R^{18}O$    $OR^{19}$
        \  /
(z)     —C—         ;

Z is $CH_2$, O, $NR^{13}$ or S;

—A—B—C—D— represents the constituent atoms of a 6-member saturated or unsaturated heterocyclic ring with the pyrrole to which they are attached containing 1 to 3 nitrogen atoms and includes the following:

1) —C=C—C=N—,
       |   |   |
       $R^7$ $R^7$ $R^7$

2) —N=C—C=C—,
       |   |   |
       $R^7$ $R^7$ $R^7$

3) —C=C—N=C—,
       |   |      |
       $R^7$ $R^7$  $R^7$

4) —C=N—C=C—,
       |      |   |
       $R^7$   $R^7$ $R^7$

5) —C=C—N=N—,
       |   |
       $R^7$ $R^7$

6) —N=N—C=C—,
             |   |
             $R^7$ $R^7$

7) 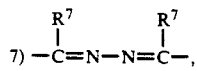
8) 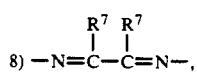
9) 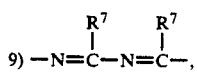
10) 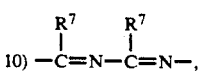
11) 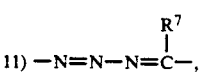
12) 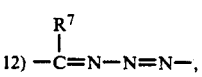
13) 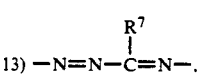
14) 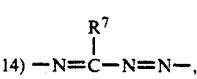
15) 
16) 
17) 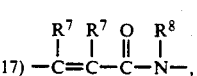
18) 
19) 
20) 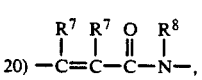
21) 
22) 
23) 
24) 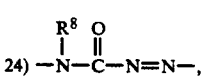
25) 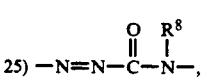
26) 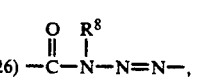
27) 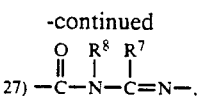
28) 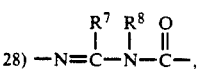
29) 
30) 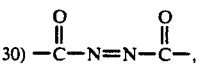
31) 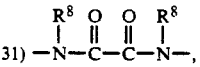
32) 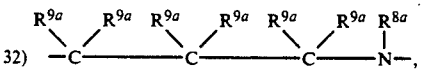
33) 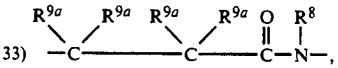
34) 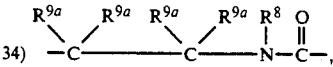
35) 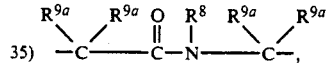
36) 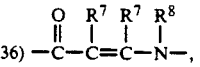
37) 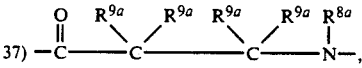
38) 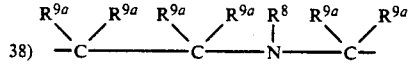
$R^7$ groups can be the same or different and represent:
a) hydrogen,
b) $C_1-C_6$ alkyl, or $C_2-C_6$ alkenyl, or $C_2-C_6$ alkynyl each of which is unsubstituted or substituted with:
  i) —OH
  ii) $C_1-C_4$-alkoxy,
  iii) —$CO_2R^4$,
  iv) —$OCOR^4$,
v) 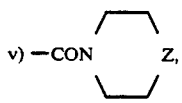
vi) —$CON(R^4)_2$
vii) 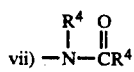
viii) —$N(R^4)_2$,
ix) aryl,
x) heterocyclic as defined in (o) below,
xi) —$S(O)_xR^{23}$,
xii) tetrazol-5-yl,
xiii) —$CONHSO_2R^{23}$, xiv) —SO$_2$NH-heteroaryl,
xv) —SO$_2$NHCOR$^{23}$, xvi) 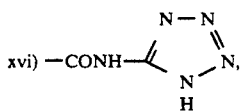

xvii) 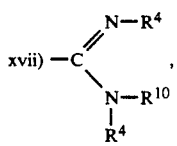

xviii) 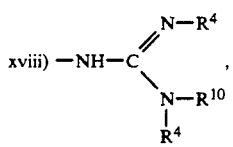

xix) —PO(OR$^4$)$_2$,
xx) —PO(OR$^4$)R$^9$,
c) chloro, bromo or iodo,
d) perfluoro-C$_1$-C$_4$-alkyl,
e) —OH,
f) —NH$_2$, g) 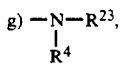

h) 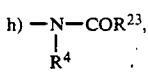

i) —OR$^{23}$,
j) —CO$_2$R$^4$,
k) —CON(R$^4$)$_2$,
l) —NH—C$_3$-C$_7$-cycloalkyl,
m) C$_3$-C$_7$-cycloalkyl,
n) aryl, or
o) heterocyclic which is a five- or six-membered saturated or unsaturated ring containing up to three heteroatoms selected from the group consisting of O, N or S wherein S may in the form of sulfoxide or sulfone or a substituted heterocyclic with one or two substituents which are members selected from the group consisting of Cl, Br, F, I, C$_1$-C$_4$-alkyl, C$_1$-C$_4$-alkoxy, C$_1$-C$_4$—S(O)$_x$—, CF$_3$, NO$_2$, OH, CO$_2$H, CO$_2$—C$_1$-C$_4$-alkyl, or —N(R$^4$)$_2$;
p) —CN, q) (CH$_2$)$_n$ N— wherein n is 4 to 6, r) —SO$_2$N(R$^4$)$_2$;
s) tetrazol-5-yl,
t) —CONHSO$_2$R$^{23}$,
u) —PO(OR$^4$)$_2$,
v) —NHSO$_2$CF$_3$,
w) —SO$_2$NH-heteroaryl,
x) —SO$_2$NHCOR$^{23}$,
y) —S(O)$_x$—R$^{23}$, z) 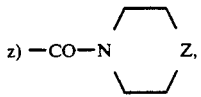

aa) —PO(OR$^4$)R$^9$,
bb) —NHSO$_2$R$^{23}$,
cc) —NHSO$_2$NHR$^{23}$,
dd) —NHSO$_2$NHCOR$^{23}$,
ee) —NHCONHSO$_2$R$^{23}$,
ff) —N(R$^4$)CO$_2$R$^{23}$, gg) 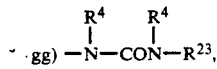

hh) —CO-aryl, ii) 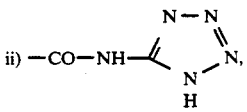

jj) —CO—C$_1$-C$_4$-alkyl,
kk) —SO$_2$NH-CN, ll) 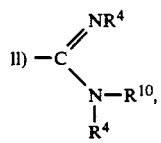

mm) 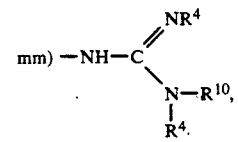

nn) 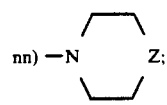

R$^8$ groups can be the same or different and represent:
a) hydrogen,
b) C$_1$-C$_6$-alkyl or C$_2$-C$_6$alkenyl either unsubstituted or substituted with aryl, hydroxy, C$_1$-C$_4$-alkoxy, —N(R$^4$)$_2$, —CO$_2$R$^4$, or C$_3$-C$_5$-cycloalkyl;
c) C$_3$-C$_5$-cycloalkyl,
R$^{8a}$ is R$^8$ or C$_1$-C$_4$-acyl;
R$^{9a}$ groups can be the same or different and represent:
a) hydrogen,
b) C$_1$-C$_6$-alkyl either unsubstituted or substituted with
i) hydroxy,
ii) —CO$_2$R$^4$,
iii) —CONHR$^4$, or
iv) —CON(R$^4$)$_2$;
and, the pharmaceutically acceptable salts thereof.

The terms "alkyl", "alkenyl", "alkynyl" and the like include both the straight chain and branched chain species of these generic terms wherein the number of carbon atoms in the species permit. Unless otherwise noted, the specific names for these generic terms shall mean the straight chain species. For example, the term "butyl" shall mean the normal butyl substituent, n-butyl.

One embodiment of this invention is the class compounds of Formula I wherein:

$R^1$ is:
a) $-CO_2R^4$
b) $-NHSO_2CF_3$

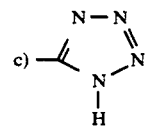

c)

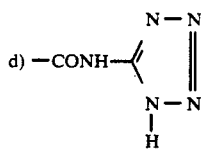

d) $-CONH-$ (e) $-SO_2NH$-heteroaryl,
(f) $-CH_2SO_2NH$-heteroaryl,
(g) $-SO_2NHCOR^{23}$,
(h) $-CH_2SO_2NHCOR^{23}$,
(i) $-CONHSO_2R^{23}$,
(j) $-CH_2CONHSO_2R^{23}$,
(k) $-NHSO_2NHCOR^{23}$,
(l) $-NHCONHSO_2R^{23}$, or
(m) $-SO_2NHCONHR^{23}$;

X is a single bond;

$R^{2a}$ and $R^{2b}$ are independently:
a) $C_1$-$C_4$-alkyl,
b) halogen, or
c) hydrogen;

$R^{3a}$ and $R^{3b}$ are independently:
a) $C_1$-$C_6$-alkyl,
b) halogen,
c) $C_1$-$C_6$-alkoxy, or
d) hydrogen;

$R^4$ is H, or $C_1$-$C_4$-alkyl;

E is a single bond or $-S-$;

$R^6$ is $C_1$-$C_6$-alkyl, $C_3$-$C_7$-cycloalkyl, $C_2$-$C_6$-alkenyl or $C_2$-$C_6$-alkynyl each of which is either unsubstituted or substituted with $C_1$-$C_4$-alkylthio, $C_1$-$C_4$-alkoxy, $CF_3$, $-CF_2CF_3$ or $-CF_2CH_2CH_3$;

and A—B—C—D— represents:

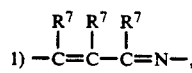
1)

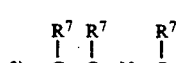
2)

3)

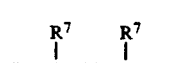
4)

5)

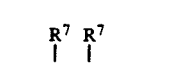
6)

-continued

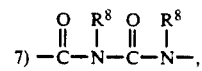
7)

8)

9)

10)

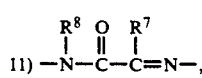
11)

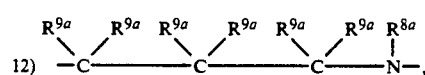
12)

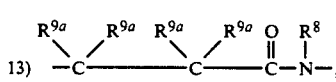
13)

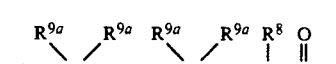
14)

$R^7$ groups are the same or different and represent:
a) hydrogen,
b) $-C_1$-$C_4$-alkyl, either unsubstituted or substituted with:
   i) $-OH$,
   ii) $-CO_2R^4$,
   iii) $-NH_2$,
   iv) ($C_1$-$C_4$ alkyl)amino,
   v) di($C_1$-$C_4$-alkyl)amino,
c) halo,
d) $-CF_3$,
e) $-OH$,
f) $-N(R^4)_2$,
g) $-C_1$-$C_4$-alkoxy,
h) $-CO_2R^4$,
i) $-CONH_2$,
j) $-C_3$-$C_7$-cycloalkyl,
k) aryl,
l) heterocyclic,
m) $-CF_3$,
n) tetrazol-5-yl,
o) $-CONHSO_2R^{23}$;

$R^8$ groups are the same or different and represent,
a) hydrogen,
b) $C_1$-$C_4$-alkyl either unsubstituted or substituted with $-OH$ or $-CO_2R^4$; and $R^{8a}$ represents
a) hydrogen,
b) $C_1$-$C_4$ alkyl, or
c) ($C_1$-$C_4$-alkyl)CO—;

$R^{9a}$ groups are the same or different and represent:
a) hydrogen,
b) $C_1$-$C_4$-alkyl; and $R^{24}$ is
a) hydrogen,
b) $C_1$-$C_6$-alkyl,
c) $C_3$-$C_7$-cycloalkyl,
d) cyclopropylmethyl,
e) $-CF_3$, f) —OH.

In a class of this embodiment are those compounds of Formula (I) wherein:

$R^1$ is (a) —$CO_2R^4$, (b) 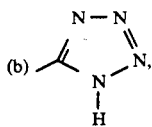

(c) —$NHSO_2CF_3$,
(d) —$SO_2NH$-heteroaryl,
(e) —$CH_2SO_2NH$-heteroaryl,
(f) —$SO_2NHCOR^{23}$,
(g) —$CH_2SO_2NHCOR^{23}$,
(h) —$CONHSO_2R^{23}$,
(i) —$CH_2CONHSO_2R^{23}$;

E is a single bond;

A—B—C—D represents:

1) 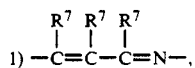

2) 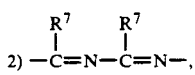

3) 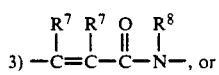, or

4) 

One subclass of this embodiment is represented by the compounds of the following formula (II):

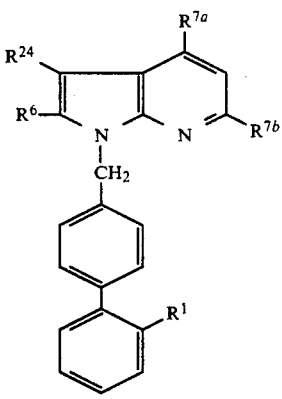

wherein:

$R^1$ is (a) —$CO_2R^4$,
(b) —$NHSO_2CF_3$, (c) 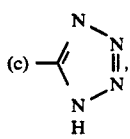

(d) —$CONHSO_2Ph$, (e) —$CONHSO_2Ph$-2-Br,
(f) —$SO_2NHCOPh$, or
(g) —$SO_2NHCO$cyclopropyl;

$R^4$ is hydrogen or $C_1$-$C_4$ alkyl;
$R^6$ is $C_1$-$C_6$ alkyl, $C_2$-$C_6$ alkenyl or $C_3$-$C_7$ cycloalkyl;
$R^{7a}$ and $R^{7b}$ independently are
 (a) hydrogen,
 (b) $C_1$-$C_4$-alkyl,
 (c) substituted $C_1$-$C_4$ alkyl in which the substituent is
  (i) hydroxy,
  (ii) —$CO_2R^4$
  (iii) amino,
  (iv) $C_1$-$C_4$ alkylamino,
  (v) di($C_1$-$C_4$ alkyl)amino, or
 (d) $C_1$-$C_4$ alkoxy; and
$R^{24}$ is hydrogen, $C_1$-$C_6$ alkyl or $C_3$-$C_7$ cycloalkyl.

Illustrating this subclass are the compounds of the formula (II) wherein:

$R^1$ is (a) —$CO_2R^4$, or (b) 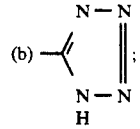

$R^4$ is hydrogen or $C_1$-$C_4$ alkyl;
$R^6$ is $C_1$-$C_6$ alkyl, or $C_3$-$C_7$ cycloalkyl;
$R^{7a}$ and $R^{7b}$ independently are
 (a) hydrogen,
 (b) $C_1$-$C_6$ alkyl, or
 (c) —$CO_2R^4$; and
$R^{24}$ is hydrogen or $C_1$-$C_6$ alkyl.

A second subclass of this embodiment is represented by the compounds of the following formula (III):

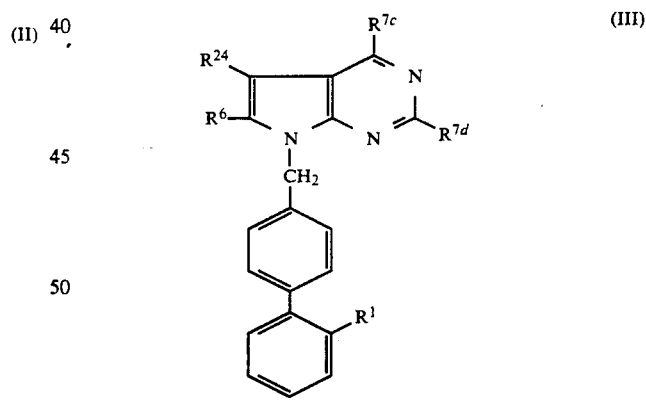

wherein:

$R^1$ is (a) —$CO_2R^4$ (b) 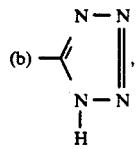

(c) —$SO_2NHCOPh$, or
(d) —$SO_2NHCO$ cyclopropyl;

$R^4$ is hydrogen or $C_1$-$C_4$ alkyl;

$R^6$ is $C_1$-$C_6$ alkyl, $C_2$-$C_6$ alkenyl or $C_3$-$C_7$ cycloalkyl;

$R^{7c}$ and $R^{7d}$ independently are (a) hydrogen, (b) $C_1$-$C_4$ alkyl, (c) substituted $C_1$-$C_4$ alkyl in which the substituent is (i) hydroxy, (ii) —$CO_2R^4$ (iii) amino, (iv) $C_1$-$C_4$ alkylamino, or (v) di($C_1$-$C_4$ alkyl)amino, (d) —$CO_2R^4$, (e) —$CONHR^4$, (f) —$CON(R^4)_2$, (g) amino, (h) $C_1$-$C_4$ alkylamino, (i) di($C_1$-$C_4$ alkyl)amino or

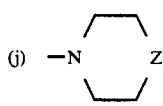

in which Z is $CH_2$, O, S or N—$C_1$-$C_6$ alkyl; and $R^{24}$ is hydrogen, $C_1$-$C_6$ alkyl or $C_3$-$C_7$ cycloalkyl.

Illustrating this subclass are the compounds of the formula (III) wherein:

$R^1$ is (a) —$CO_2R^4$, or

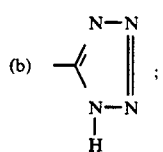

$R^4$ is hydrogen or $C_1$-$C_4$ alkyl;

$R^6$ is $C_1$-$C_6$ alkyl or $C_{3-7}$ cycloalkyl;

$R^{7c}$ and $R^{7d}$ independently are (a) hydrogen (b) $C_1$-$C_4$ alkyl, (c) —$CO_2R^4$, (d) $C_1$-$C_4$ alkylamino, (e) di($C_1$-$C_4$ alkyl)amino, or (f) morpholino; and $R^{24}$ is hydrogen or $C_1$-$C_6$ alkyl.

A third subclass of this embodiment is represented by the compounds of the following formula (IV):

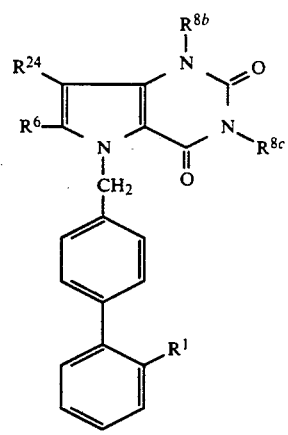

wherein:

$R^1$ is (a) —$CO_2R^4$,

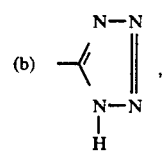

(b) —$SO_2NHCOPh$, or (c) —$SO_2NHCO$cyclopropyl;

$R^4$ is hydrogen or $C_1$-$C_4$ alkyl;

$R^6$ is $C_1$-$C_6$ alkyl, $C_2$-$C_6$ alkenyl or $C_3$-$C_7$ cycloalkyl;

$R^{8b}$ and $R^{8c}$ independently are (a) hydrogen, (b) $C_1$-$C_6$ alkyl, or (c) $C_2$-$C_6$ alkenyl; and $R^{24}$ is hydrogen, $C_1$-$C_6$ alkyl or $C_3$-$C_7$ cycloalkyl.

A fourth subclass of this embodiment is represented by the compounds of the following formula (V):

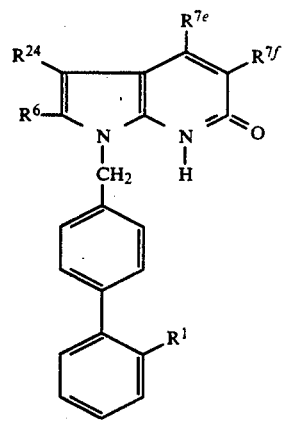

wherein:

$R^1$ is (a) —$CO_2R^4$, (b) 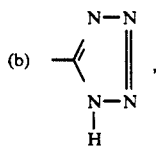

(c) —SO$_2$NHCOPh, or
(d) —SO$_2$NHCO cyclopropyl;

R$^4$ is hydrogen or C$_1$–C$_4$ alkyl;
R$^6$ is C$_1$–C$_6$ alkyl, C$_2$–C$_6$ alkyl or C$_3$–C$_7$ cycloalkyl;
R$^{7e}$ and R$^{7f}$ independently are
  (a) hydrogen,
  (b) C$_1$–C$_4$ alkyl, or
  (c) substituted alkyl in which the substituent is
    (i) hydroxy,
    (ii) —CO$_2$R$^4$,
    (iii) amino,
    (iv) C$_1$–C$_4$ alkylamino,
    (v) di(C$_1$–C$_4$ alkyl)amino, or
    (vi) alkoxy; and
R$^{24}$ is hydrogen or C$_1$–C$_6$ alkyl.

Exemplifying this class are the following compounds:
(1) 2-propyl-1-[(2'-carboxy-[1,1']-biphenyl-4-yl)methyl]-1H-pyrrolo[2,3-b]pyridine;
(2) 2-butyl-4-methyl-1-[(2'-carboxy-[1,1']-biphenyl-4-yl)methyl]-1H-pyrrolo[2,3-b]-pyridine;
(3) 2-cyclopropyl-4-methyl-1-[(2'-carboxy-[1,1']-biphenyl-4-yl)methyl]-1H-pyrrolo[2,3-b]pyridine;
(4) 2-ethyl-4-methyl-1-[(2'-carboxy-[1,1']-biphenyl-4-yl)methyl]-1H-pyrrolo[2,3-b]-pyridine;
(5) 4,6-dimethyl-2-ethyl-1-[(2'-carboxy-[1,1']-biphenyl-4-yl)methyl]-1H-pyrrolo[2,3-b]-pyridine;
(6) 4,6-dimethyl-2-propyl-1-[(2'-carboxy-[1,1']-biphenyl-4-yl)methyl]-1H-pyrrolo[2,3-b]-pyridine;
(7) 2-cyclopropyl-4,6-dimethyl-1-[(2'-carboxy-[1,1']-biphenyl-4-yl)methyl]-1H-pyrrolo-[2,3-b]pyridine;
(8) 2-butyl-4,6-dimethyl-1-[(2'-carboxy-[1,1']-biphenyl-4-yl)methyl]-1H-pyrrolo[2,3-b]-pyridine;
(9) 6-ethyl-4-methyl-2-propyl-1-[(2'-carboxy-[1,1']-biphenyl-4-yl)methyl]-1H-pyrrolo-[2,3-b]pyridine;
(10) 2,6-dipropyl-4-methyl-1-[(2'-carboxy-[1,1']-biphenyl-4-yl)methyl]-1H-pyrrolo[2,3-b]-pyridine;
(11) 4-methyl-2-propyl-1-[(2'-carboxy-[1,1']-biphenyl-4-yl)methyl]-1H-pyrrolo[2,3-b]-pyridine;
(12) 2-ethyl-4-methyl-1-[(2'-carboxy-[1,1']-biphenyl-4-yl)methyl]-1H-pyrrolo[2,3-b]-pyridine-6-carboxylic acid;
(13) 4-methyl-2-propyl-1-[(2'-carboxy-[1,1']-biphenyl-4-yl)methyl]-1H-pyrrolo[2,3-b]-pyridine-6-carboxylic acid;
(14) 2-cyclopropyl-4-methyl-1-[(2'-carboxy-[1,1']-biphenyl-4-yl)methyl]-1H-pyrrolo-[2,3-b]pyridine-6-carboxylic acid;
(15) 2-butyl-4-methyl-1-[(2'-carboxy-[1,1']-biphenyl-4-yl)methyl]-1H-pyrrolo[2,3-b]-pyridine-6-carboxylic acid;
(16) 2-ethyl-4-methyl-1-[(2'-carboxy-[1,1']-biphenyl-4-yl)methyl]-1H-pyrrolo[2,3-b]-pyridine-6-carboxylic acid ethyl ester;
(17) 4-methyl-2-propyl-1-[(2'-carboxy-[1,1']-biphenyl-4-yl)methyl]-1H-pyrrolo[2,3-b]-pyridine-6-carboxylic acid ethyl ester;
(18) 2-cyclopropyl-4-methyl-1-[(2'-carboxy-[1,1']-biphenyl-4-yl)methyl]-1H-pyrrolo-[2,3-b]pyridine-6-carboxylic acid ethyl ester;
(19) 2-butyl-4-methyl-1-[(2'-carboxy-[1,1']-biphenyl-4-yl)methyl]-1H-pyrrolo[2,3-b]-pyridine-6-carboxylic acid ethyl ester;
(20) 4-methyl-2-propyl-1-[(2'-carboxy-[1,1']-biphenyl-4-yl)methyl]-1H-pyrrolo[2,3-b]-pyridine-6-carboxylic acid benzyl ester;
(21) 4-methyl-2-propyl-1-[[2'-(1H-tetrazol-5-yl)-[1,1']-biphenyl-4-yl]methyl]-1H-pyrrolo-[2,3-b]pyridine;
(22) 2-butyl-4-methyl-1-[[2'-(1H-tetrazol-5-yl)-[1,1']-biphenyl-4-yl]methyl]-1H-pyrrolo[2,3-b]pyridine;
(23) 2-cyclopropyl-4-methyl-1-[[2'-(1H-tetrazol-5-yl)[1,1']-biphenyl-4-yl]methyl]-1H-pyrrolo[2,3-b]pyridine;
(24) 2-ethyl-4-methyl-1-[[2'-(1H-tetrazol-5-yl)-[1,1']-biphenyl-4-yl]methyl]-1H-pyrrolo[2,3-b]pyridine;
(25) 4,6-dimethyl-2-ethyl-1-[[2'-(1H-tetrazol-5-yl)[1,1']-biphenyl-4-yl]methyl]-1H-pyrrolo-[2,3-b]pyridine;
(26) 4,6-dimethyl-2-propyl-1-[[2'-(1H-tetrazol-5-yl)[1,1']-biphenyl-4-yl]methyl]-1H-pyrrolo-[2,3-b]pyridine;
(27) 2-cyclopropyl-4,6-dimethyl-1-[[2'-(1H-tetrazol-5-yl)[1,1']-biphenyl-4-yl]methyl]-1H-pyrrolo[2,3-b]pyridine;
(28) 2-butyl-4,6-dimethyl-1-[[2'-(1H-tetrazol-5-yl)[1,1']-biphenyl-4-yl]methyl]-1H-pyrrolo-[2,3-b]pyridine;
(29) 6-ethyl-4-methyl-2-propyl-1-[[2'-(1H-tetrazol-5-yl)[1,1']-biphenyl-4-yl]methyl]-1H-pyrrolo[2,3-b]pyridine;
(30) 2,6-dipropyl-4-methyl-1-[[2'-(1H-tetrazol-5-yl)[1,1']-biphenyl-4-yl]methyl]-1H-pyrrolo-[2,3-b]pyridine;
(31) 2-propyl-1-[[2'-(1H-tetrazol-5-yl)[1,1']-biphenyl-4-yl]methyl]-1H-pyrrolo[2,3-b]-pyridine;
(32) 2-ethyl-4-methyl-1-[[2'-(1H-tetrazol-5-yl)-[1,1']-biphenyl-4-yl]methyl]-1H-pyrrolo-[2,3-b]pyridine-6-carboxylic acid;
(33) 4-methyl-2-propyl-1-[[2'-(1H-tetrazol-5-yl)-[1,1']-biphenyl-4-yl]methyl]-1H-pyrrolo-[2,3-b]pyridine-6-carboxylic acid;
(34) 2-cyclopropyl-4-methyl-1-[[2'-(1H-tetrazol-5-yl)[1,1']-biphenyl-4-yl]methyl]-1H-pyrrolo-[2,3-b]pyridine-6-carboxylic acid;
(35) 2-butyl-4-methyl-1-[[2'-(1H-tetrazol-5-yl)-[1,1']-biphenyl-4-yl]methyl]-1H-pyrrolo-[2,3-b]pyridine-6-carboxylic acid;
(36) 2-ethyl-4-methyl-1-[[2'-(1H-tetrazol-5-yl)-[1,1']-biphenyl-4-yl]methyl]-1H-pyrrolo-[2,3-b]pyridine-6-carboxylic acid ethyl ester;
(37) 4-methyl-2-propyl-1-[[2'-(1H-tetrazol-5-yl)-[1,1']-biphenyl-4-yl]methyl]-1H-pyrrolo-[2,3-b]pyridine-6-carboxylic acid ethyl ester;
(38) 2-cyclopropyl-4-methyl-1-[[2'-(1H-tetrazol-5-yl)[1,1']-biphenyl-4-yl]methyl]-1H-pyrrolo-[2,3-b]pyridine-6-carboxylic acid ethyl ester;
(39) 2-butyl-4-methyl-1-[[2'-(1H-tetrazol-5-yl)-[1,1']-biphenyl-4-yl]methyl]-1H-pyrrolo-[2,3-b]pyridine-6-carboxylic acid ethyl ester;
(40) 4-methyl-2-propyl-1-[[2'-(1H-tetrazol-5-yl)-[1,1']-biphenyl-4-yl]methyl]-1H-pyrrolo-[2,3-b]pyridine-6-carboxylic acid benzyl ester;
(41) 1,7-dihydro-4,6-dimethyl-2-ethyl-1-[[2'-(1H-tetrazol-5-yl)[1,1']-biphenyl-4-yl]methyl]-6H-pyrrolo[2,3-b]pyridin-6-one;
(42) 1,7-dihydro-4,6-dimethyl-2-propyl-1-[[2'-(1H-tetrazol-5-yl)[1,1']-biphenyl-4-yl]methyl]-6H-pyrrolo[2,3-b]pyridin-6-one;

(43) 4-methyl-2-propyl-1-[[(2'-trifluormethylsulfonamido)[1,1']-biphen-4-yl]methyl]-1H-pyrrolo[2,3-b]pyridine;
(44) 2-butyl-4-methyl-1-[[(2'-trifluormethylsulfonamido)[1,1']-biphen-4-yl]methyl]-1H-pyrrolo[2,3-b]pyridine;
(45) 2-cyclopropyl-4-methyl-1-[[(2'-trifluoromethylsulfonamido)[1,1']-biphen-4-yl]methyl]-1H-pyrrolo[2,3-b]pyridine;
(46) 2-ethyl-4-methyl-1-[[[(2'-trifluormethylsulfonamido)[1,1']-biphen-4-yl]methyl]-1H-pyrrolo[2,3-b]pyridine;
(47) 4,6-dimethyl-2-ethyl-1-[[(2'-trifluormethylsulfonamido)[1,1']-biphen-4-yl]methyl]-1H-pyrrolo[2,3-b]pyridine;
(48) 4,6-dimethyl-2-propyl-1-[[(2'-trifluoromethylsulfonamido)[1,1']-biphen-4-yl]methyl]-1H-pyrrolo[2,3-b]pyridine;
(49) 2-cyclopropyl-4,6-dimethyl-1-[[(2'-trifluoromethylsulfonamido)[1,1']-biphen-4-yl]methyl]-1H-pyrrolo[2,3-b]pyridine;
(50) 2-butyl-4,6-dimethyl-1-[[(2'-trifluoromethylsulfonamido)[1,1']-biphen-4-yl]methyl]-1H-pyrrolo[2,3-b]pyridine;
(51) 6-ethyl-4-methyl-2-propyl-1-[[(2'-trifluoromethylsulfonamido)[1,1']-biphen-4-yl]methyl]-1H-pyrrolo[2,3-b]pyridine;
(52) 2,6-dipropyl-4-methyl-1-[[(2'-trifluoromethylsulfonamido)[1,1']-biphen-4-yl]methyl]-1H-pyrrolo[2,3-b]pyridine;
(53) 2,6-dibutyl-4-methyl-1-[[(2'-trifluoromethylsulfonamido)[1,1']-biphen-4-yl]methyl]-1H-pyrrolo[2,3-b]pyridine;
(54) 2-ethyl-4-methyl-1-[[(2'-trifluoromethylsulfonamido)[1,1']-biphen-4-yl]methyl]-1H-pyrrolo[2,3-b]pyridine-6-carboxylic acid;
(55) 4-methyl-2-propyl-1-[[(2'-trifluoromethylsulfonamido)[1,1']-biphen-4-yl]methyl]-1H-pyrrolo[2,3-b]pyridine-6-carboxylic acid;
(56) 2-cyclopropyl-4-methyl-1-[[(2'-trifluoromethylsulfonamido)[1,1']-biphen-4-yl]methyl]-1H-pyrrolo[2,3-b]pyridine-6-carboxylic acid;
(57) 2-butyl-4-methyl-1-[[(2'-trifluoromethylsulfonamido)[1,1']-biphen-4-yl]methyl]-1H-pyrrolo[2,3-b]pyridine-6-carboxylic acid;
(58) 2-ethyl-4-methyl-1-[[(2'-trifluoromethylsulfonamido)[1,1']-biphen-4-yl]methyl]-1H-pyrrolo[2,3-b]pyridine-6-carboxylic acid ethyl ester;
(59) 4-methyl-2-propyl-1-[[(2'-trifluoromethylsulfonamido)[1,1']-biphen-4-yl]methyl]-1H-pyrrolo[2,3-b]pyridine-6-carboxylic acid ethyl ester;
(60) 2-cyclopropyl-4-methyl-1-[[(2'-trifluoromethylsulfonamido)[1,1']-biphen-4-yl]methyl]-1H-pyrrolo[2,3-b]pyridine-6-carboxylic acid ethyl ester;
(61) 2-butyl-4-methyl-1-[[(2'-trifluoromethylsulfonamido)[1,1']-biphen-4-yl]methyl]-1H-pyrrolo[2,3-b]pyridine-6-carboxylic acid ethyl ester;
(62) 4-methyl-2-propyl-1-[[(2'-trifluoromethylsulfonamido)[1,1']-biphen-4-yl]methyl]-1H-pyrrolo[2,3-b]pyridine-6-carboxylic acid benzyl ester;
(63) 4-methyl-2-propyl-1-[2'-(N-(phenylsulfonyl)-carboxamido)-[1,1']-biphen-4-yl]methyl-1H-pyrrolo[2,3-b]pyridine;
(64) 2-butyl-4-methyl-1-[2'-(N-(phenylsulfonyl)-carboxamido)-[1,1']-biphen-4-yl]methyl-1H-pyrrolo[2,3-b]pyridine;
(65) 2-cyclopropyl-4-methyl-1-[2'-(N-(phenylsulfonyl)-carboxamido)-[1,1']-biphen-4-yl]-methyl-1H-pyrrolo[2,3-b]pyridine;
(66) 2-ethyl-4-methyl-1-[2'-(N-(phenylsulfonyl)-carboxamido)-[1,1']-biphen-4-yl]methyl-1H-pyrrolo[2,3-b]pyridine;
(67) 4,6-dimethyl-2-ethyl-1-[2'-(N-(phenylsulfonyl)carboxamido)-[1,1']-biphen-4-yl]-methyl-1H-pyrrolo[2,3-b]pyridine;
(68) 4,6-dimethyl-2-propyl-1-[2'-(N-(phenylsulfonyl)-carboxamido)-[1,1']-biphen-4-yl]-methyl-1H-pyrrolo[2,3-b]pyridine;
(69) 2-cyclopropyl-4,6-dimethyl-1-[2'-(N-(phenylsulfonyl)carboxamido)-[1,1']-biphen-4-yl]-methyl-1H-pyrrolo[2,3-b]pyridine;
(70) 2-butyl-4,6-dimethyl-1-[2'-(N-(phenylsulfonyl)carboxamido)-[1,1']-biphen-4-yl]-methyl-1H-pyrrolo[2,3-b]pyridine;
(71) 6-ethyl-4-methyl-2-propyl-1-[2'-(N-(phenylsulfonyl)carboxamido)-[1,1']-biphen-4-yl]-methyl-1H-pyrrolo[2,3-b]pyridine;
(72) 2,6-dipropyl-4-methyl-1-[2'-(N-(phenylsulfonyl)-carboxamido)-[1,1']-biphen-4-yl]-methyl-1H-pyrrolo[2,3-b]pyridine;
(73) 2,6-dibutyl-4-methyl-1-[2'-(N-(phenylsulfonyl)carboxamido)-[1,1']-biphen-4-yl]-methyl-1H-pyrrolo[2,3-b]pyridine;
(74) 2-ethyl-4-methyl-1-[2'-(N-(phenylsulfonyl)carboxamido)-[1,1']-biphen-4-yl]methyl-1H-pyrrolo[2,3-b]pyridine-6-carboxylic acid;
(75) 4-methyl-2-propyl-1-[2'-(N-(phenylsulfonyl)-carboxamido)-[1,1']-biphen-4-yl]methyl-1H-pyrrolo[2,3-b]pyridine-6-carboxylic acid;
(76) 2-cyclopropyl-4-methyl-[2'-(N-(phenylsulfonyl)-carboxamido)-[1,1']-biphen-4-yl]-methyl-1H-pyrrolo[2,3-b]pyridine-6-carboxylic acid;
(77) 2-butyl-4-methyl-1-[2'-(N-(phenylsulfonyl)-carboxamido)-[1,1']-biphen-4-yl]methyl-1H-pyrrolo[2,3-b]pyridine-6-carboxylic acid;
(78) 2-ethyl-4-methyl-1-[2'-(N-(phenylsulfonyl)-carboxamido)-[1,1']-biphen-4-yl]methyl-1H-pyrrolo[2,3-b]pyridine-6-carboxylic acid ethyl ester;
(79) 4-methyl-2-propyl-1-[2'-(N-(phenylsulfonyl)-carboxamido)-[1,1']-biphen-4-yl]methyl-1H-pyrrolo[2,3-b]pyridine-6-carboxylic acid ethyl ester;
(80) 2-cyclopropyl-4-methyl-1-[2'-(N-(phenylsulfonyl)-carboxamido)-[1,1']-biphen-4-yl]-methyl-1H-pyrrolo[2,3-b]pyridine-6-carboxylic acid ethyl ester;
(81) 2-butyl-4-methyl-1-[2'-(N-(phenylsulfonyl)-carboxamido)-[1,1']-biphen-4-yl]methyl-1H-pyrrolo[2,3-b]pyridine-6-carboxylic acid ethyl ester;
(82) 4-methyl-2-propyl-1-[2'-(N-(2-bromophenylsulfonyl)carboxamido)-[1,1']-biphen-4-yl]-methyl-1H-pyrrolo[2,3-b]pyridine;
(83) 2-butyl-4-methyl-1-[2'-(N-(2-bromophenylsulfonyl)carboxamido)-[1,1']-biphen-4-yl]-methyl-1H-pyrrolo[2,3-b]pyridine;
(84) 2-cyclopropyl-4-methyl-1-[2'-(N-(2-bromophenylsulfonyl)carboxamido)-[1,1']-biphen-4-yl]methyl-1H-pyrrolo[2,3-b]pyridine;
(85) 2-ethyl-4-methyl-1-[2'-(N-(2-bromophenylsulfonyl)carboxamido)-[1,1']-biphen-4-yl]-methyl-1H-pyrrolo[2,3-b]pyridine;
(86) 4,6-dimethyl-2-ethyl-1-[2'-(N-(2-bromophenylsulfonyl)carboxamido)-[1,1']-biphen-4-yl]-methyl-1H-pyrrolo[2,3-b]pyridine;

(87) 4,6-dimethyl-2-propyl-1-[2'-(N-(2-bromophenylsulfonyl)carboxamido)-[1,1']-biphen-4-yl]methyl-1H-pyrrolo[2,3-b]pyridine;
(88) 2-cyclopropyl-4,6-dimethyl-1-[2'-(N-(2-bromophenylsulfonyl)carboxamido)-[1,1']-biphen-4-yl]methyl-1H-pyrrolo[2,3-b]pyridine;
(89) 2-butyl-4,6-dimethyl-1-[2'-(N-(2-bromophenylsulfonyl)carboxamido)-[1,1']-biphen-4-yl]-methyl-1H-pyrrolo[2,3-b]pyridine;
(90) 6-ethyl-4-methyl-2-propyl-1-[2'-(N-(2-bromophenylsulfonyl)carboxamido)-[1,1']-biphen-4-yl]methyl-1H-pyrrolo[2,3-b]pyridine;
(91) 2,6-dipropyl-4-methyl-1-[2'-(N-(2-bromophenylsulfonyl)carboxamido)-[1,1']-biphen-4-yl]methyl-1H-pyrrolo[2,3-b]pyridine;
(92) 2,6-dibutyl-4-methyl-1-[2'-(N-(2-bromophenylsulfonyl)carboxamido)-[1,1']-biphen-4-yl]-methyl-1H-pyrrolo[2,3-b]pyridine;
(93) 2-ethyl-4-methyl-1-[2'-(N-(2-bromophenylsulfonyl)carboxamido)-[1,1']-biphen-4-yl]-methyl-1H-pyrrolo[2,3-b]pyridine-6-carboxylic acid;
(94) 4-methyl-2-propyl-1-[2'-(N-(2-bromophenylsulfonyl)carboxamido)-[1,1']-biphen-4-yl]-methyl-1H-pyrrolo[2,3-b]pyridine-6-carboxylic acid;
(95) 2-cyclopropyl-4-methyl-[2'-(N-(2-bromophenylsulfonyl)carboxamido)-[1,1']-biphen-4-yl]-methyl-1H-pyrrolo[2,3-b]pyridine-6-carboxylic acid;
(96) 2-butyl-4-methyl-1-[2'-(N-(2-bromophenylsulfonyl)carboxamido)-[1,1']-biphen-4-yl]-methyl-1H-pyrrolo[2,3-b]pyridine-6-carboxylic acid;
(97) 2-ethyl-4-methyl-1-[2'-(N-(2-bromophenylsulfonyl)carboxamido)-[1,1']-biphen-4-yl]-methyl-1H-pyrrolo[2,3-b]pyridine-6-carboxylic acid ethyl ester;
(98) 4-methyl-2-propyl-1-[2'-(N-(2-bromophenylsulfonyl)carboxamido)-[1,1']-biphen-4-yl]-methyl-1H-pyrrolo[2,3-b]pyridine-6-carboxylic acid ethyl ester;
(99) 2-cyclopropyl-4-methyl-1-[2'-(N-(2-bromophenylsulfonyl)carboxamido)-[1,1']-biphen-4-yl]methyl-1H-pyrrolo[2,3-b]pyridine-6-carboxylic acid ethyl ester;
(100) 2-butyl-4-methyl-1-[2'-(N-(2-bromophenylsulfonyl)carboxamido)-[1,1']-biphen-4-yl]-methyl-1H-pyrrolo[2,3-b]pyridine-6-carboxylic acid ethyl ester;
(101) 4-methyl-2-propyl-1-[2'-(N-benzoyl)sulfonamido-[1,1']-biphen-4-yl]methyl-1H-pyrrolo[2,3-b]pyridine;
(102) 2-butyl-4-methyl-1-[2'-(N-benzoyl)sulfonamido-[1,1']-biphen-4-yl]methyl-1H-pyrrolo[2,3-b]pyridine;
(103) 2-cyclopropyl-4-methyl-1-[2'-(N-benzoyl)-sulfonamido-[1,1']-biphen-4-yl]methyl-1H-pyrrolo[2,3-b]pyridine;
(104) 2-ethyl-4-methyl-1-[2'-(N-benzoyl)-sulfonamido-[1,1']-biphen-4-yl]methyl-1H-pyrrolo[2,3-b]pyridine;
(105) 4,6-dimethyl-2-ethyl-1-[2'-(N-benzoyl)-sulfonamido-[1,1']-biphen-4-yl]methyl-1H-pyrrolo[2,3-b]pyridine;
(106) 4,6-dimethyl-2-propyl-1-[2'-(N-benzoyl)-sulfonamido-[1,1']-biphen-4-yl]methyl-1H-pyrrolo[2,3-b]pyridine;
(107) 2-cyclopropyl-4,6-dimethyl-1-[2'-(N-benzoyl)-sulfonamido-[1,1']-biphen-4-yl]methyl-1H-pyrrolo[2,3-b]pyridine;
(108) 2-butyl-4,6-dimethyl-1-[2'-(N-benzoyl)-sulfonamido-[1,1']-biphen-4-yl]methyl-1H-pyrrolo[2,3-b]pyridine;
(109) 6-ethyl-4-methyl-2-propyl-1-[2'-(N-benzoyl)-sulfonamido-[1,1']-biphen-4-yl]methyl-1H-pyrrolo[2,3-b]pyridine;
(110) 2,6-dipropyl-4-methyl-1-[2'-(N-benzoyl)-sulfonamido-[1,1']-biphen-4-yl]methyl-1H-pyrrolo[2,3-b]pyridine;
(111) 2,6-dibutyl-4-methyl-1-[2'-(N-benzoyl)-sulfonamido-[1,1']-biphen-4-yl]methyl-1H-pyrrolo[2,3-b]pyridine;
(112) 2-ethyl-4-methyl-1-[2'-(N-benzoyl)-sulfonamido-[1,1']-biphen-4-yl]methyl-1H-pyrrolo[2,3-b]pyridine-6-carboxylic acid;
(113) 4-methyl-2-propyl-1-[2'-(N-benzoyl)-sulfonamido-[1,1']-biphen-4-yl]methyl-1H-pyrrolo[2,3-b]pyridine-6-carboxylic acid;
(114) 2-cyclopropyl-4-methyl-[2'-(N-benzoyl)-sulfonamido-[1,1']-biphen-4-yl]methyl-1H-pyrrolo[2,3-b]pyridine-6-carboxylic acid;
(115) 2-butyl-4-methyl-1-[2'-(N-benzoyl)-sulfonamido-[1,1']-biphen-4-yl]methyl-1H-pyrrolo[2,3-b]pyridine-6-carboxylic acid;
(116) 2-ethyl-4-methyl-1-[2'-(N-benzoyl)-sulfonamido-[1,1']-biphen-4-yl]methyl-1H-pyrrolo[2,3-b]pyridine-6-carboxylic acid ethyl ester;
(117) 4-methyl-2-propyl-1-[2'-(N-benzoyl)-sulfonamido-[1,1']-biphen-4-yl]methyl-1H-pyrrolo[2,3-b]pyridine-6-carboxylic acid ethyl ester;
(118) 2-cyclopropyl-4-methyl-1-[2'-(N-benzoyl)-sulfonamido-[1,1']-biphen-4-yl]methyl-1H-pyrrolo[2,3-b]pyridine-6-carboxylic acid ethyl ester;
(119) 2-butyl-4-methyl-1-[2'-(N-cyclopropanecarbonyl)sulfonamido-[1,1']-biphen-4-yl]-methyl-1H-pyrrolo[2,3-b]pyridine-6-carboxylic acid ethyl ester;
(120) 1,7-dihydro-4,6-dimethyl-2-ethyl-1-[2'-(N-benzoyl)sulfonamido-[1,1']-biphen-4-yl]-methyl-6H-pyrrolo[2,3-b]pyridin-6-one;
(121) 1,7-dihydro-4,6-dimethyl-2-propyl-1-[2'-(N-benzoyl)sulfonamido-[1,1']-biphen-4-yl]-methyl-6H-pyrrolo[2,3-b]pyridin-6-one;
(122) 4-methyl-2-propyl-1-[2'-(N-cyclopropanecarbonyl)sulfonamido-[1,1']-biphen-4-yl]-methyl-1H-pyrrolo[2,3-b]pyridine
(123) 2-butyl-4-methyl-1-[2'-(N-cyclopropanecarbonyl)sulfonamido-[1,1']-biphen-4-yl]-methyl-1H-pyrrolo[2,3-b]pyridine;
(124) 2-cyclopropyl-4-methyl-1-[2'-(N-cyclopropanecarbonyl)sulfonamido-[1,1']-biphen-4-yl]-methyl-1H-pyrrolo[2,3-b]pyridine;
(125) 2-ethyl-4-methyl-1-[2'-(N-cyclopropanecarbonyl)sulfonamido-[1,1']-biphen-4-yl]-methyl-1H-pyrrolo[2,3-b]pyridine;
(126) 4,6-dimethyl-2-ethyl-1-[2'-(N-cyclopropanecarbonyl)-sulfonamido-[1,1']-biphen-4-yl]-methyl-1H-pyrrolo[2,3-b]pyridine;
(127) 4,6-dimethyl-2-propyl-1-[2'-(N-cyclopropanecarbonyl)sulfonamido-[1,1']-biphen-4-yl]-methyl-1H-pyrrolo[2,3-b]pyridine;
(128) 2-cyclopropyl-4,6-dimethyl-1-[2'-(N-cyclopropanecarbonyl)sulfonamido-[1,1']-biphen-4-yl]methyl-1H-pyrrolo[2,3-b]pyridine;
(129) 2-butyl-4,6-dimethyl-1-[2'-(N-cyclopropanecarbonyl)sulfonamido-[1,1']-biphen-4-yl]-methyl-1H-pyrrolo[2,3-b]pyridine;
(130) 6-ethyl-4-methyl-2-propyl-1-[2'-(N-cyclopropanecarbonyl)sulfonamido-[1,1']-biphen-4-yl]methyl-1H-pyrrolo[2,3-b]pyridine;
(131) 2,6-dipropyl-4-methyl-1-[2'-(N-cyclopropanecarbonyl)sulfonamido-[1,1']-biphen-4-yl]-methyl-1H-pyrrolo[2,3-b]pyridine;

(132) 2,6-dibutyl-4-methyl-1-[2'-(N-cyclopropanecarbonyl)sulfonamido-[1,1']-biphen-4-yl]-methyl-1H-pyrrolo[2,3-b]pyridine;
(133) 2-ethyl-4-methyl-1-[2'-(N-cyclopropanecarbonyl)sulfonamido-[1,1']-biphen-4-yl]-methyl-1H-pyrrolo[2,3-b]pyridine-6-carboxylic acid;
(134) 4-methyl-2-propyl-1-[2'-(N-cyclopropanecarbonyl)sulfonamido-[1,1']-biphen-4-yl]-methyl-1H-pyrrolo[2,3-b]pyridine-6-carboxylic acid;
(135) 2-cyclopropyl-4-methyl-[2'-(N-cyclopropanecarbonyl)sulfonamido-[1,1']-biphen-4-yl]-methyl-1H-pyrrolo[2,3-b]pyridine-6-carboxylic acid;
(136) 2-butyl-4-methyl-1-[2'-(N-cyclopropanecarbonyl)sulfonamido-[1,1']-biphen-4-yl]-methyl-1H-pyrrolo[2,3-b]pyridine-6-carboxylic acid;
(137) 2-ethyl-4-methyl-1-[2'-(N-cyclopropanecarbonyl)sulfonamido-[1,1']-biphen-4-yl]-methyl-1H-pyrrolo[2,3-b]pyridine-6-carboxylic acid ethyl ester;
(138) 4-methyl-2-propyl-1-[2'-(N-cyclopropanecarbonyl)sulfonamido-[1,1']-biphen-4-yl]-methyl-1H-pyrrolo[2,3-b]pyridine-6-carboxylic acid ethyl ester;
(139) 2-cyclopropyl-4-methyl-1-[2'-(N-cyclopropanecarbonyl)sulfonamido-[1,1']-biphen-4-yl]-methyl-1H-pyrrolo[2,3-b]pyridine-6-carboxylic acid ethyl ester;
(140) 2-butyl-4-methyl-1-[2'-(N-cyclopropanecarbonyl)sulfonamido-[1,1']-biphen-4-yl]-methyl-1H-pyrrolo[2,3-b]pyridine-6-carboxylic acid ethyl ester;
(141) 6-cyclopropyl-4-methyl-7-[[2'-(1H-tetrazol-5-yl)[1,1']-biphenyl-4-yl]methyl]-1H-pyrrolo-[2,3-d]pyrimidine;
(142) 6-propyl-4-methyl-7-[[2'-(1H-tetrazol-5-yl)-[1,1']-biphenyl-4-yl]methyl]-1H-pyrrolo-[2,3-d]pyrimidine;
(143) 6-ethyl-4-methyl-7-[[2'-(1H-tetrazol-5-yl)-[1,1']-biphenyl-4-yl]methyl]-1H-pyrrolo-[2,3-d]pyrimidine;
(144) 2,4-dimethyl-6-ethyl-7-[[2'-(1H-tetrazol-5-yl)[1,1']-biphenyl-4-yl]methyl]-1H-pyrrolo-[2,3-d]pyrimidine;
(145) 2,4-dimethyl-6-propyl-7-[[2'-(1H-tetrazol-5-yl)[1,1']-biphenyl-4-yl]methyl]-1H-pyrrolo-[2,3-d]pyrimidine;
(146) 6-cyclopropyl-2,4-dimethyl-7-[[2'-(1H-tetrazol-5-yl)[1,1']-biphenyl-4-yl]methyl]-1H-pyrrolo[2,3-d]pyrimidine;
(147) 2-dimethylamino-4-methyl-6-propyl-7-[[2'-(1H-tetrazol-5-yl)[1,1']-biphenyl-4-yl]methyl]-1H-pyrrolo[2,3-d]pyrimidine;
(148) 2-methylamino-4-methyl-6-propyl-7-[[2'-(1H-tetrazol-5-yl)[1,1']-biphenyl-4-yl]methyl]-1H-pyrrolo[2,3-d]pyrimidine;
(149) 2-morpholino-4-methyl-6-propyl-7-[[2'-(1H-tetrazol-5-yl)[1,1']-biphenyl-4-yl]methyl]-1H-pyrrolo[2,3-d]pyrimidine;
(150) 2-dimethylamino-4-methyl-6-ethyl-7-[[2'-(1H-tetrazol-5-yl)[1,1']-biphenyl-4-yl]methyl]-1H-pyrrolo[2,3-d]pyrimidine;
(151) 2-methylamino-4-methyl-6-ethyl-7-[[2'-(1H-tetrazol-5-yl)[1,1']-biphenyl-4-yl]methyl]-1H-pyrrolo[2,3-d]pyrimidine;
(152) 2-morpholino-4-methyl-6-ethyl-7-[[2'-(1H-tetrazol-5-yl)[1,1']-biphenyl-4-yl]methyl]-1H-pyrrolo[2,3-d]pyrimidine;
(153) 6-ethyl-4-methyl-7-[[2'-(1H-tetrazol-5-yl)-[1,1']-biphenyl-4-yl]methyl]-1H-pyrrolo-[2,3-d]pyrimidine-2-carboxylic acid;
(154) 4-methyl-6-propyl-7-[[2'(1H-tetrazol-5-yl)-[1,1']-biphenyl-4-yl]methyl]-1H-pyrrolo-[2,3-d]pyrimidine-2-carboxylic acid;
(155) 6-cyclopropyl-4-methyl-7-[[2'-(1H-tetrazol-5-yl)[1,1']-biphenyl-4-yl]methyl]-1H-pyrrolo-[2,3-d]pyrimidine-2-carboxylic acid;
(156) 6-butyl-4-methyl-7-[[2'-(1H-tetrazol-5-yl)-[1,1']-biphenyl-4-yl]methyl]-1H-pyrrolo-[2,3-d]pyrimidine-2-carboxylic acid;
(157) 6-ethyl-4-methyl-7-[[2'-(1H-tetrazol-5-yl)-[1,1']-biphenyl-4-yl]methyl]-1H-pyrrolo-[2,3-d]pyrimidine-2-carboxylic acid ethyl ester;
(158) 4-methyl-6-propyl-7-[[2'-(1H-tetrazol-5-yl)-[1,1']-biphenyl-4-yl]methyl]-1H-pyrrolo-[2,3-d]pyrimidine-2-carboxylic acid ethyl ester;
(159) 6-cyclopropyl-4-methyl-7-[[2'-(1H-tetrazol-5-yl)[1,1']-biphenyl-4-yl]methyl]-1H-pyrrolo-[2,3-d]pyrimidine-2-carboxylic acid ethyl ester;
(160) 2,4-dimethyl-6-ethyl-1-[2'-(N-benzoyl)-sulfonamido-[1,1']-biphen-4-yl]-methyl-1H-pyrrolo[2,3-b]pyrimidine;
(161) 2-dimethylamino-6-ethyl-4-methyl-1-[2'-(N-benzoyl)sulfonamido-[1,1']-biphen-4-yl]-methyl-1H-pyrrolo[2,3-b]pyrimidine;
(162) 6-ethyl-4-methyl-2-(N-morpholino)-1-[2'-(N-benzoyl)sulfonamido-[1,1']-biphen-4-yl]-methyl-1H-pyrrolo[2,3-b]pyrimidine;
(163) 2,4-dimethyl-6-propyl-7-[2'-(N-benzoyl)-sulfonamido-[1,1']-biphenyl-4-yl]methyl-1H-pyrrolo[2,3-d]pyrimidine;
(164) 6-cyclopropyl-2,4-dimethyl-7-[2'-(N-benzoyl)-sulfonamido-[1,1']-biphenyl-4-yl]methyl-1H-pyrrolo[2,3-d]pyrimidine;
(165) 6-ethyl-4-methyl-7-[2'-(N-benzoyl)-sulfonamido-[1,1']-biphenyl-4-yl]methyl-1H-pyrrolo[2,3-d]pyrimidine-2-carboxylic acid;
(166) 4-methyl-6-propyl-7-[2'-(N-benzoyl)-sulfonamido-[1,1']-biphenyl-4-yl]methyl-1H-pyrrolo[2,3-d]pyrimidine-2-carboxylic acid;
(167) 6-cyclopropyl-4-methyl-7-[2'-(N-benzoyl)-sulfonamido-[1,1']-biphenyl-4-yl]methyl-1H-pyrrolo[2,3-d]pyrimidine-2-carboxylic acid;
(168) 6-butyl-4-methyl-7-[2'-(N-benzoyl)-sulfonamido-[1,1']-biphenyl-4-yl]methyl-1H-pyrrolo[2,3-d]pyrimidine-2-carboxylic acid;
(169) 6-ethyl-4-methyl-7-[2'-(N-benzoyl)-sulfonamido-[1,1']-biphenyl-4-yl]methyl-1H-pyrrolo[2,3-d]pyrimidine-2-carboxylic acid ethyl ester;
(170) 4-methyl-6-propyl-7-[2'-(N-benzoyl)-sulfonamido-[1,1']-biphenyl-4-yl]methyl-1H-pyrrolo[2,3-d]pyrimidine-2-carboxylic acid ethyl ester;

The compounds of Formula (I) can be synthesized using the reactions and techniques described herein below. The reactions are performed in a solvent appropriate to the reagents and materials employed and suitable for the transformation being effected. It is understood by those skilled in the art of organic synthesis that the functionality present on the heterocycle and in the reactants being employed should be consistent with the chemical transformations being conducted. Depending upon the reactions and techniques employed, optimal yields may require changing the order of synthetic steps or use of protecting groups followed by deprotection.

| ABBREVIATIONS USED IN REACTION SCHEMES | |
|---|---|
| Reagents: | |
| NBS | N-bromosuccinimide |
| AIBN | Azo(bis)isobutyronitrile |
| DDQ | Dichlorodicyanoquinone |
| Ac₂O | acetic anhydride |

ABBREVIATIONS USED IN REACTION SCHEMES

| | |
|---|---|
| TEA | triethylamine |
| DMAP | 4-dimethylaminopyridine |
| PPh$_3$ | triphenylphosphine |
| TFA | trifluoroacetic acid |
| TMS—Cl | trimethylsilyl chloride |
| Im | imidazole |
| AcSK | potassium thioacetate |
| p-TsOH | p-toluenesulfonic acid |
| Solvents: | |
| Et$_2$O | diethyl ether |
| DMF | dimethylformamide |
| HOAc (AcOH) | acetic acid |
| EtOAc (EtAc) | ethyl acetate |
| Hex | hexane |
| THF | tetrahydrofuran |
| DMSO | dimethylsulfoxide |
| MeOH | methanol |
| iPrOH | isopropanol |
| DBU | 1,8-diazabicyclo-[5.4.0]undec-7-ene |
| Me$_3$SnCl | trimethylstannyl chloride |
| Others: | |
| rt | room temperature |
| TBDMS | t-butyldimethylsilyl |
| OTf | OSO$_2$CF$_3$ |
| OTs | OSO$_2$-(4-methyl)phenyl |
| OMs | OSO$_2$CH$_3$ |
| Ph | phenyl |
| FAB-MS (FABMS) | Fast atom bombardment mass spectroscopy |
| NOE | Nuclear Overhauser Effect |
| SiO$_2$ | silica gel |
| trityl | triphenylmethyl |

As shown in Reaction Scheme 1, compounds of Formula I can be prepared by carrying out direct alkylation of alkali-metal salts of heterocycles (1) (preparation of heterocycles are described in Schemes 3–6) using appropriately protected benzyl halide, tosylate (OTs) or mesylate (OMs) derivatives (2). The salt is prepared preferably using MH (where M is lithium, sodium or potassium) in anhydrous dimethylformamide (DMF), or by treating the heterocycle with a metal alkoxide such as sodium or potassium methoxide, ethoxide or t-butoxide in an appropriate alcohol such as methanol, ethanol or t-butanol as the solvent. The alkylation is generally carried out by dissolving the metal salt of the heterocycle in a dipolar aprotic solvent such as DMF or dimethylsulfoxide (DMSO) and reacting it with the alkylating agent at 0° C. to reflux temperature of the solvent for 1–24 hours.

SCHEME 1

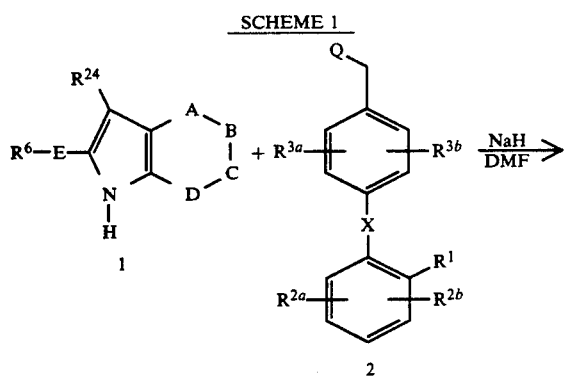

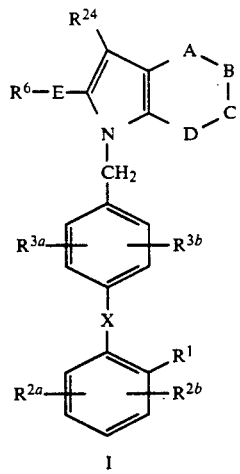

where Q=halo(I, Br, Cl), —O—tosyl, —O—mesyl.

When there is potential for alkylation in the 6-membered heterocyclic ring, this can be avoided by the use of suitable protecting groups.

The substituted benzyl halides (2) including the specific alkylation agents (3), (4), (5), and (5a) shown in Scheme 2 can be prepared as described in European Patent Application 400,974 and references therein.

SCHEME 2

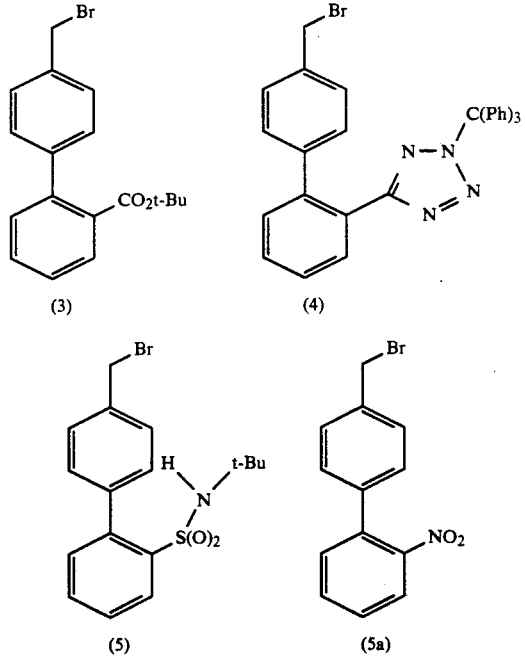

The heterocycles of type (1) can be prepared by any of the standard procedures described in the literature [J. V. Greenhill in "Comprehensive Heterocyclic Chemistry," Vol. 4, A. R. Katritsky and C. W. Reese Eds., Pergamon Press 1984; pp 502–529 and references cited therein and R. J. Sundberg in "Comprehensive Heterocyclic Chemistry", Vol. 4, A. R. Katritsky and C. W. Reese Eds., Pergamon Press 1984; pp 314–368 and references cited therein.]. As shown in Scheme 3 the Madelung synthesis and variations thereof provides pyrroles with b-fused rings (7) and (9) from ortho-methyl aryl amides (6) or amidines (8).

Ketones or aldehydes such as (12) can be prepared from orthomethylaryl nitro compounds (10) via hydrolysis of enamines (11) as shown in Scheme 4. Heterocycles (1) are obtained from (12) upon reduction of the nitro group. Scheme 5 shows the preparation of heterocycles (1) via a Tschitschibabin type reaction on heteroaryl alkenes (13). An alternative approach is the direct displacement reaction on (14) by $NH_3$ or a metal salt thereof, or azide or hydrazine followed by reduction to the amine. Both of these reaction types yield dihydropyrrole type intermediates which are aromatized under the reaction conditions or in a separate step with oxidizing agents such as $O_2$, DDQ, or chloranil.

Installation of $R^6$ after preparation of the heterocycle can be accomplished via a deprotonation-alkylation process as shown in Scheme 6. The starting heterocycle (15) is N-protected by reaction with sodium hydride followed by benzenesulfonyl chloride to give (16) which in turn can be treated with strong base such as n-BuLi followed by an alkyl halide to give (17). Removal of the benzenesulfonyl group gives heterocycle (1).

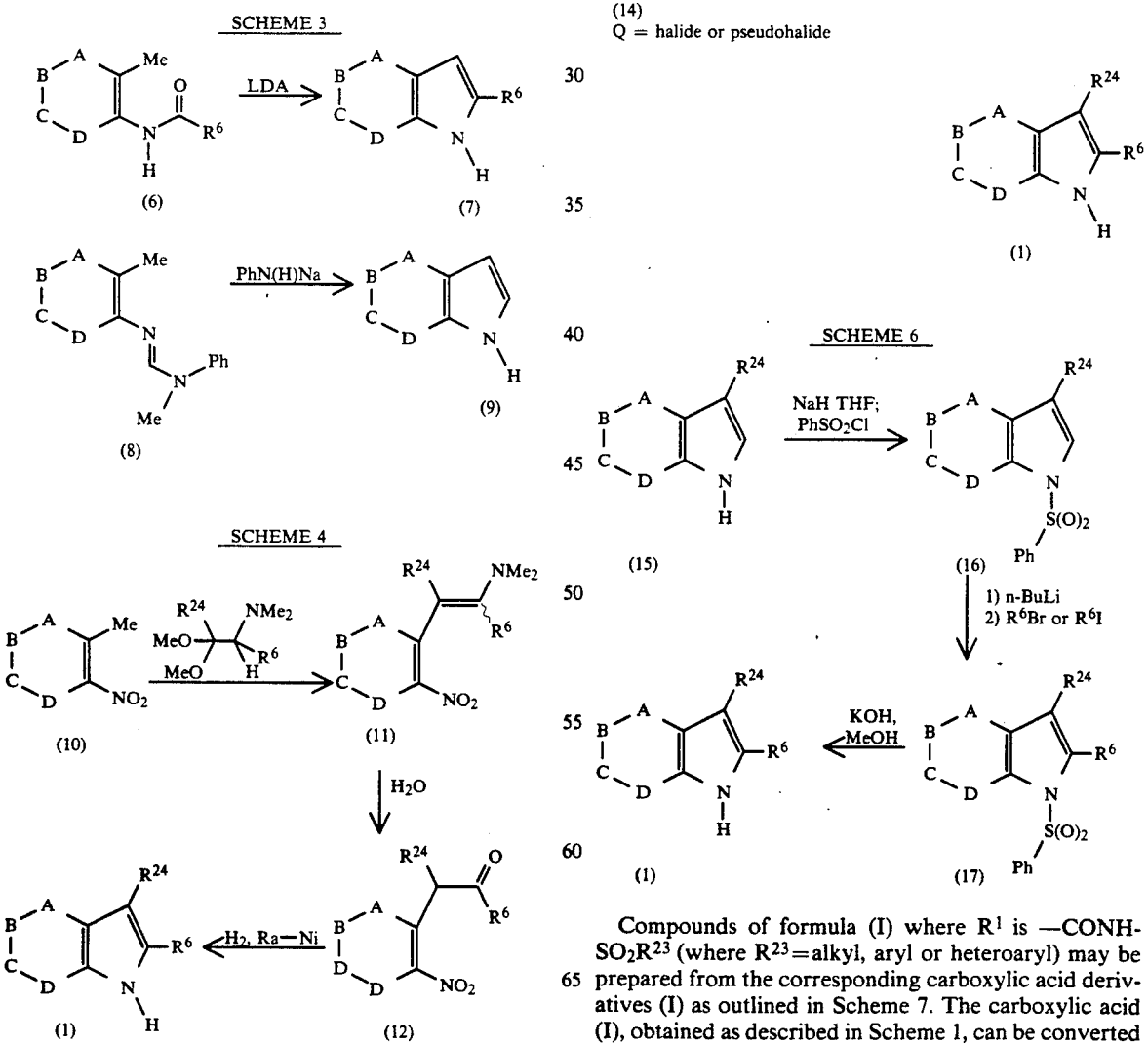

Compounds of formula (I) where $R^1$ is —CONH-$SO_2R^{23}$ (where $R^{23}$=alkyl, aryl or heteroaryl) may be prepared from the corresponding carboxylic acid derivatives (I) as outlined in Scheme 7. The carboxylic acid (I), obtained as described in Scheme 1, can be converted into the corresponding acid chloride by treatment with refluxing thionyl chloride or preferably with oxalyl chloride and a catalytic amount of dimethylformamide at low temperature [A. W. Burgstahler, L. O. Weigel, and C. G. Shaefer—*Synthesis*, 767, (1976)]. The acid chloride then can be treated with the alkali metal salt of $R^{23}SO_2NH_2$ to form the desired acylsulfonamide (18).

Alternatively, these acylsulfonamides may be also prepared from the carboxylic acids using N,N-diphenylcarbamoyl anhydride intermediates [F. J. Brown et al—European Patent Application, EP 199543; K. L. Shepard and W. Halczenko—*J. Het. Chem.*, 16, 321 (1979)]. Preferably the carboxylic acids can be converted into acyl-imidazole intermediates, which then can be treated with an appropriate aryl or alkylsulfonamide and diazabicycloundecane (DBU) to give the desired acylsulfonamide (26) [J. T. Drummond and G. Johnson—*Tetra. Lett.*, 29, 1653 (1988)].

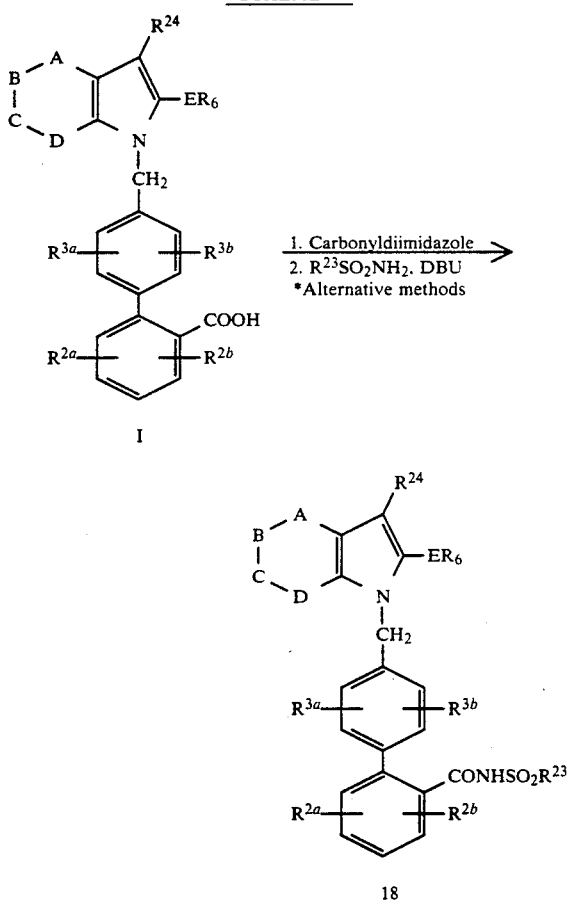

*Alternative Methods:
a) (i) $SOCl_2$, reflux
   (ii) $R^{23}SO_2NH^-M^+$ (where M is Na or Li)

b) (i) $(COCl)_2$—DMF, $-20°$ C.
   (ii) $R^{23}SO_2NH^-M^+$ c) (i) N(N,N-Diphenylcarbamoyl)pyridinium chloride/Aq. NaOH
   (ii) $R^{23}SO_2NH^-M^+$.

Compounds of formula I where $R^1$ is —$SO_2NH$-$COR^{23}$ may be prepared as outlined in Scheme 8. The benzylbromide (5) can be reacted with an alkali metal salt of an appropriate heterocyclic compound (1) to form an intermediate t-butylsulfonamide adduct which in turn is treated with trifluroacetic acid to remove the t-butyl group thus forming (19). The acylation of (19) with appropriate acyl chlorides (or acyl-imidazoles or other acylating agents) may produce the desired acylsulfonamides (20).

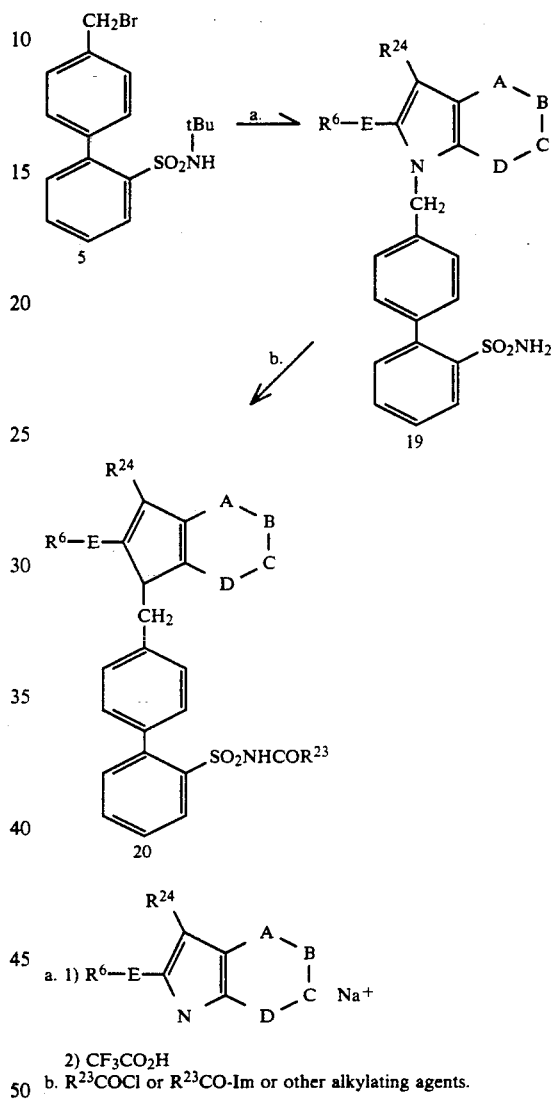

a. 1) $R^6$—E—[structure] $Na^+$
   2) $CF_3CO_2H$
b. $R^{23}COCl$ or $R^{23}CO$-Im or other alkylating agents.

The compounds of the Formula (I) wherein $R^1$ is —$NHSO_2CF_3$ are prepared from the compounds of the Formula (I) wherein $R^1$ is —$NO_2$ (derived from Compound 5a) by reduction of the nitro group with $H_2/Pd$—C or $H_2/Ra$—Ni followed by treatment with $(CF_3SO_2)_2O$ and 2,6-di-t-butylpyridine in methylene chloride.

It will be appreciated by those skilled in the art that functional group transformations can be conducted on aryl and heterocyclic rings to afford desired analogs. For example, esters may be converted to amides by heating them with amines and an amide nitrogen if present in the heterocycle may be alkylated using bases such as sodium hydride in DMF with the appropriate alkyl halide. Functional group protection throughout these syntheses will be chosen to be compatible with subsequent reaction conditions. Ultimately such protecting groups will be removed to generate the desired optimally active compounds of Formula (I). For example, $R^1$ as carboxyl is often protected as its t-butyl ester which in the last step is removed by treatment with trifluoroacetic acid. Aqueous acetic acid at room temperature overnight or HCl in methanol are preferred methods to remove a trityl protecting group to liberate an $R^1$ tetrazole group.

The compounds of this invention form salts with various inorganic and organic acids and bases which are also within the scope of the invention. Such salts include ammonium salts, alkali metal salts like sodium and potassium salts, alkaline earth metal salts like the calcium and magnesium salts, salts with organic bases; e.g., dicyclohexylamine salts, N-methyl-D-glucamine, salts with amino acids like arginine, lysine, and the like. Also, salts with organic and inorganic acids may be prepared; e.g., HCl, HBr, $H_2SO_4$, $H_3PO_4$, methane-sulfonic, toluenesulfonic, maleic, fumaric, camphorsulfonic. The non-toxic, physiologically, acceptable salts are preferred, although other salts are also useful; e.g., in isolating or purifying the product.

The salts can be formed by conventional means such as by reacting the free acid or free base forms of the product with one or more equivalents of the appropriate base or acid in a solvent or medium in which the salt is insoluble, or in a solvent such as water which is then removed in vacuo or by freeze-drying or by exchanging the cations of an existing salt for another cation on a suitable ion exchange resin.

Angiotensin II (AII) is a powerful arterial vasoconstrictor, and it exerts its action by interacting with specific receptors present on cell membranes. The compounds described in the present invention act as competitive antagonists of AII at the receptors. In order to identify AII antagonists and determine their efficacy in vitro, the following two ligand-receptor binding assays were established.

Receptor Binding Assay Using Rabbit Aortae Membrane Preparation

Three frozen rabbit aortae (obtained from Pel-Freeze Biologicals) were suspended in 5 mM Tris-0.25M Sucrose, pH 7.4 buffer (50 ml) homogenized, and then centrifuged. The mixture was filtered through a cheesecloth and the supernatant was centrifuged for 30 minutes at 20,000 rpm at 4° C. The pellet thus obtained was resuspended in 30 ml of 50 mM Tris-5 mM $MgCl_2$ buffer containing 0.2% Bovine Serum Albumin and 0.2 mg/ml Bacitration and the suspension was used for 100 assay tubes. Samples tested for screening were done in duplicate. To the membrane preparation (0.25 ml) there was added $^{125}$I-Sar$^1$Ile$^8$-angiotensin II [obtained from New England Nuclear] (10 ul; 20,000 cpm) with or without the test sample and the mixture was incubated at 37° C. for 90 minutes. The mixture was then diluted with ice-cold 50 mM Tris-0.9% NaCl, pH 7.4 (4 ml) and filtered through a glass fiber filter (GF/B Whatman 2.4" diameter). The filter was soaked in scintillation cocktail (10 ml) and counted for radioactivity using Packard 2660 Tricarb liquid scintillation counter. The inhibitory concentration ($IC_{50}$) of potential AII antagonist which gives 50% displacement of the total specifically bound $^{125}$I-Sar$^1$Ile$^8$-angiotensin II was presented as a measure of the efficacy of such compounds as AII antagonists.

Receptor Assay Using Bovine Adrenal Cortex Preparation

Bovine adrenal cortex was selected as the source of AII receptor. Weighed tissue (0.1 g is needed for 100 assay tubes) was suspended in Tris.HCl (50 mM), pH 7.7 buffer and homogenized. The homogenate was centrifuged at 20,000 rpm for 15 minutes. Supernatant was discarded and pellets resuspended in buffer [$Na_2HPO_4$ (10 mM)-NaCl (120 mM)-disodium EDTA (5 mM) containing phenylmethane sulfonyl fluoride (PMSF) (0.1 mM)]. (For screening of compounds, generally duplicates of tubes are used). To the membrane preparation (0.5 ml) there was added 3H-angiotensin II (50 mM) (10 ul) with or without the test sample and the mixture was incubated at 37° C. for 1 hour. The mixture was then diluted with Tris buffer (4 ml) and filtered through a glass fiber filter (GF/B Whatman 2.4" diameter). The filter was soaked in scintillation cocktail (10 ml) and counted for radioactivity using Packard 2660 Tricarb liquid scintillation counter. The inhibitory concentration ($IC_{50}$) of potential AII antagonist which gives 50% displacement of the total specifically bound $^3$H-angiotensin II was presented as a measure of the efficacy of such compounds as AII antagonists.

The antihypertensive effects of the compounds described in the present invention may be evaluated using the methodology described below:

Male Charles River Sprague-Dawley rats (300–375 gm) were anesthetized with methohexital (Brevital; 50 mg/kg i.p.) and the trachea was cannulated with PE 205 tubing. A stainless steel pithing rod (1.5 mm thick, 150 mm long) was inserted into the orbit of the right eye and down the spinal column. The rats were immediately placed on a Harvard Rodent Ventilator (rate—60 strokes per minute, volumn—1.1 cc per 100 grams body weight). The right carotid artery was ligated, both left and right vagal nerves were cut, and the left carotid artery was cannulated with PE 50 tubing for drug administration, and body temperature was maintained at 37° C. by a thermostatically controlled heating pad which received input from a rectal temperature probe. Atropine (1 mg/kg i.v.) was then administered, and 15 minutes later propranolol (1 mg/kg i.v.). Thirty minutes later angiotensin II or other agonists were administered intravenously at 30-minute intervals and the increase in the diastolic blood pressure was recorded before and after drug or vehicle administration.

Using the methodology described above, representative compounds of this invention were evaluated and were found to exhibit an activity of at least $IC_{50}<50$ μM, thereby demonstrating and confirming the utility of the compounds of the invention as effective AII antagonists.

The compounds of the invention are useful in treating hypertension. They are also of value in the management of acute and chronic congestive heart failure. These compounds may also be expected to be useful in the treatment of secondary hyperaldosteronism, primary and secondary pulmonary hyperaldosteronism, primary and secondary pulmonary hypertension, renal failure such as diabetic nephropathy, glomerulonephritis, scleroderma, glomerular sclerosis, proteinuria of primary renal disease, end stage renal disease, renal transplant therapy, and the like, renal vascular hypertension, left ventricular dysfunction, diabetic retinopathy and in the management of vascular disorders such as migraine, Raynaud's disease, luminal hyperclasia, and to minimize the atherosclerotic process. The application of the compounds of this invention for these and similar disorders will be apparent to those skilled in the art.

The compounds of this invention are also useful to treat elevated intraocular pressure and to enhance retinal blood flow and can be administered to patients in need of such treatment with typical pharmaceutical formulations such as tablets, capsules, injectables and the like as well as topical ocular formulations in the form of solutions, ointments, inserts, gels, and the like. Pharmaceutical formulations prepared to treat intraocular pressure would typically contain about 0.1% to 15% by weight, preferably 0.5% to 2% by weight, of a compound of this invention.

In the management of hypertension and the clinical conditions noted above, the compounds of this invention may be utilized in compositions such as tablets, capsules or elixirs for oral administration, suppositories for rectal administration, sterile solutions or suspensions for parenteral or intramuscular administration, and the like. The compounds of this invention can be administered to patients (animals and human) in need of such treatment in dosages that will provide optimal pharmaceutical efficacy. Although the dose will vary from patient to patient depending upon the nature and severity of disease, the patient's weight, special diets then being followed by a patient, concurrent medication, and other factors which those skilled in the art will recognize, the dosage range will generally be about 1 to 1000 mg. per patient per day which can be administered in single or multiple doses. Preferably, the dosage range will be about 2.5 to 250 mg. per patient per day; more preferably about 5 to 150 mg. per patient per day.

The compounds of this invention can also be administered in combination with other antihypertensives and/or diuretics and/or angiotensin converting enzyme inhibitors and/or calcium channel blockers. For example, the compounds of this invention can be given in combination with such compounds as amiloride, atenolol, bendroflumethiazide, chlorothalidone, chlorothiazide, clonidine, cryptenamine acetates and cryptenamine tannates, deserpidine, diazoxide, guanethidene sulfate, hydralazine hydrochloride, hydrochlorothiazide, metolazone, metoprolol tartate, methyclothiazide, methyldopa, methyldopate hydrochloride, minoxidil, pargyline hydrochloride, polythiazide, prazosin, propranolol, *rauwolfia serpentina*, rescinnamine, reserpine, sodium nitroprusside, spironolactone, timolol maleate, trichlormethiazide, trimethophan camsylate, benzthiazide, quinethazone, ticrynafan, triamterene, acetazolamide, aminophylline, cyclothiazide, ethacrynic acid, furosemide, merethoxylline procaine, sodium ethacrynate, captopril, delapril hydrochloride, enalapril, enalaprilat, fosinopril sodium, lisinopril, pentopril, quinapril hydrochloride, ramapril, teprotide, zofenopril calcium, diflusinal, diltiazem, felodipine, nicardipine, nifedipine, niludipine, nimodipine, nisoldipine, nitrendipine, and the like, as well as admixtures and combinations thereof.

Typically, the individual daily dosages for these combinations can range from about one-fifth of the minimally recommended clinical dosages to the maximum recommended levels for the entities when they are given singly.

To illustrate these combinations, one of the angiotensin II antagonists of this invention effective clinically in the 2.5-250 milligrams per day range can be effectively combined at levels at the 0.5-250 milligrams per day range with the following compounds at the indicated per day dose range: hydrochlorothiazide (15-200 mg) chlorothiazide (125-2000 mg), ethacrynic acid (15-200 mg), amiloride (5-20 mg), furosemide (5-80 mg), propranolol (20-480 mg), timolol maleate (5-60 mg.), methyldopa (65-2000 mg), felodipine (5-60 mg), nifedipine (5-60 mg), and nitrendipine (5-60 mg). In addition, triple drug combinations of hydrochlorothiazide (15-200 mg) plus amiloride (5-20 mg) plus angiotensin II antagonist of this invention (3-200 mg) or hydrochlorothiazide (15-200 mg) plus timolol maleate (5-60) plus an angiotensin II antagonist of this invention (0.5-250 mg) or hydrochlorothiazide (15-200 mg) and nifedipine (5-60 mg) plus an angiotensin II antagonist of this invention (0.5-250 mg) are effective combinations to control blood pressure in hypertensive patients. Naturally, these dose ranges can be adjusted on a unit basis as necessary to permit divided daily dosage and, as noted above, the dose will vary depending on the nature and severity of the disease, weight of patient, special diets and other factors.

Typically, these combinations can be formulated into pharmaceutical compositions as discussed below.

The useful central nervous system (CNS) activities of the compounds of this invention are demonstrated and exemplified by the ensuring assays.

COGNITIVE FUNCTION ASSAY

The efficacy of these compounds to enhance cognitive function can be demonstrated in a rat passive avoidance assay in which cholinomimetics such as physostigmine and nootropic agents are known to be active. In this assay, rats are trained to inhibit their natural tendency to enter dark areas. The test apparatus used consists of two chambers, one of which is brightly illuminated and the other is dark. Rats are placed in the illuminated chamber and the elapsed time it takes for them to enter the darkened chamber is recorded. On entering the dark chamber, they receive a brief electric shock to the feet. The test animals are pretreated with 0.2 mg/kg of the muscarinic antagonist scopolamine which disrupts learning or are treated with scopolamine and the compound which is to be tested for possible reversal of the scopolamine effect. Twenty-four hours later, the rats are returned to the illuminated chamber. Upon return to the illuminated chamber, normal young rats who have been subjected to this training and who have been treated only with control vehicle take longer to re-enter the dark chamber than test animals who have been exposed to the apparatus but who have not received a shock. Rats treated with scopolamine before training do not show this hesitation when tested 24 hours later. Efficacious test compounds can overcome the disruptive effect on learning which scopolamine produces. Typically, compounds of this invention should be efficacious in this passive avoidance assay in the dose range of from about 0.1 mg/kg to about 100 mg/kg.

ANXIOLYTIC ASSAY

The anxiolytic activity of the invention compounds can be demonstrated in a conditioned emotional response (CER) assay. Diazepam is a clinically useful anxiolytic which is active in this assay. In the CER protocol, male Sprague-Dawley rats (250-350 g) are trained to press a lever on a variable interval (VI) 60 second schedule for food reinforcement in a standard operant chamber over weekly (five days per week) training sessions. All animals then receive daily 20 minute conditioning sessions, each session partitioned into alternating 5 minute light (L) and 2 minute dark (D) periods in a fixed L1D1L2D2L3 sequence. During both periods (L or D), pressing a lever delivers food pellets on a VI 60 second schedule: in the dark (D), lever presses also elicit mild footshock (0.8 mA, 0.5 sec) on an independent shock presentation schedule of VI 20 seconds. Lever pressing is suppressed during the dark periods reflecting the formation of a conditioned emotional response (CER).

Drug testing in this paradigm is carried out under extinction conditions. During extinction, animals learn that responding for food in the dark is no longer punished by shock. Therefore, response rates gradually increase in the dark periods and animals treated with an anxiolytic drug show a more rapid increase in response rate than vehicle treated animals. Compounds of this invention should be efficacious in this test procedure in the range of from about 0.1 mg/kg to about 100 mg/kg.

DEPRESSION ASSAY

The antidepressant activity of the compounds of this invention can be demonstrated in a tail suspension test using mice. A clinically useful antidepressant which serves as a positive control in this assay is desipramine. The method is based on the observations that a mouse suspended by the tail shows alternate periods of agitation and immobility and that antidepressants modify the balance between these two forms of behavior in favor of agitation. Periods of immobility in a 5 minute test period are recorded using a keypad linked to a microcomputer which allows the experimenter to assign to each animal an identity code and to measure latency, duration and frequency of immobile periods. Compounds of this invention should be efficacious in this test procedure in the range of from about 0.1 mg/kg to about 100 mg/kg.

SCHIZOPHRENIA ASSAY

The antidopaminergic activity of the compounds of this invention can be demonstrated in an apomorphine-induced sterotypy model. A clinically useful antipsychotic drug that is used as a positive control in this assay is haloperidol. The assay method is based upon the observation that stimulation of the dopaminergic system in rats produces stereotyped motor behavior. There is a strong correlation between the effectiveness of classical neuroleptic drugs to block apomorphine-induced stereotypy and to prevent schizophrenic symptoms. Stereotyped behavior induced by apomorphine, with and without pretreatment with test compounds, is recorded using a keypad linked to a microcomputer. Compounds of the invention should be efficacious in this assay in the range of from about 0.1 mg/kg to about 100 mg/kg.

In the treatment of the clinical conditions noted above, the compounds of this invention may be utilized in compositions such as tablets, capsules or elixirs for oral administration, suppositories for rectal administration, sterile solutions or suspensions for parenteral or intramuscular administration, and the like. The compounds of this invention can be administered to patients (animals and human) in need of such treatment in dosages that will provide optimal pharmaceutical efficacy. Although the dose will vary from patient to patient depending upon the nature and severity of disease, the patient's weight, special diets then being followed by a patient, concurrent medication, and other factors which those skilled in the art will recognize, the dosage range will generally be about 5 to 6000 mg. per patient per day which can be administered in single or multiple doses. Perferably, the dosage range will be about 10 to 4000 mg. per patient per day; more preferably about 20 to 2000 mg. per patient per day.

In order to obtain maximal enhancement of cognitive function, the compounds of this invention may be combined with other cognition-enhancing agents. These include acetylcholinesterase inhibitors such as heptylphysostigmine and tetrahydroacridine (THA; tacrine), muscarinic agonists such as oxotremorine, inhibitors of angiotensin-converting enzyme such as octylramipril, captopril, ceranapril, enalapril, lisinopril, fosinopril and zofenopril, centrally-acting calcium channel blockers and as nimodipine, and nootropic agents such as piracetam.

In order to achieve optimal anxiolytic activity, the compounds of this invention may be combined with other anxiolytic agents such as alprazolam, lorazepam, diazepam, and busipirone.

In order to achieve optimal antidepressant activity, combinations of the compounds of this invention with other antidepressants are of use. These include tricyclic antidepressants such as nortriptyline, amitryptyline and trazodone, and monoamine oxidase inhibitors such as tranylcypromine.

In order to obtain maximal antipsychotic activity, the compounds of this invention may be combined with other antipsychotic agents such as promethazine, fluphenazine and haloperidol.

About 1 to 100 mg. of compound or mixture of compounds of Formula (I) or a physiologically acceptable salt is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

Illustrative of the adjuvants which can be incorporated in tablets, capsules and the like are the following: a binder such as gum tragacanth, acacia, corn starch or gelatin; an excipient such as microcrystalline cellulose; a disintegrating agent such as corn starch, pregelatinized starch, alginic acid and the like; a lubricant such as magnesium stearate; a sweetening agent such as sucrose, lactose or saccharin; a flavoring agent such as peppermint, oil of wintergreen or cherry. When the unit dosage unitform is a capsule, it may contain, in addition to materials of the above type, a liquid carrier such as fatty oil. Various other materials may be present as coatings or to otherwise modify the physical form of the dosage unit. For instance, tablets may be coated with shellac, sugar or both. A syrup or elixir may contain the active compound, sucrose as a sweetening agent, methyl and propyl parabens as preservatives, a dye and a flavoring such as cherry or orange flavor.

Sterile compositions for injection can be formulated according to conventional pharmaceutical practice by dissolving or suspending the active substance in a vehicle such as water for injection, a naturally occuring vegetable oil like sesame oil, coconut oil, peanut oil, cottonseed oil, etc., or a synthetic fatty vehicle like ethyl oleate or the like. Buffers, preservatives, antioxidants and the like can be incorporated as required.

The following examples further illustrate the preparation of the compounds of Formula (I) and their incorporation into pharmaceutical compositions and, as such, are not to be considered or construed as limiting the invention recited in the appended claims.

EXAMPLE 1

Preparation of
2-propyl-1-[[2'-(1H-tetrazol-5-yl)-[1,1']-biphenyl-4-yl]methyl]-1H-pyrrolo[2,3-b]-pyridine Step 1: 1-(benzenesulfonyl)-1H-pyrrolo[2,3-b]pyridine To a stirred solution of pyrrolo[2,3-b]-pyridine (1.0 g, 8.46 mmol) in tetrahydrofuran (15 mL) at room temperature (rt) was added NaH (280 mg of an 80% dispersion in oil, 9.31 mmol) in portions. After 20 min the solution was cooled to 0° C. and benzenesulfonyl chloride (1.13 mL, 8.88 mmol) was added over 10 min. After 30 min the reaction mixture was warmed to rt and stirred for 1 h. Water (30 mL) was added and the mixture was extracted with EtOAc (40 mL). The organic layer was washed with 5% aqueous NaHCO$_3$ then dried (MgSO$_4$). Concentration and crystallization from EtOAc-hexanes gave 1-(benzenesulfonyl)-1H-pyrrolo[2,3-b]pyridine as a solid.

Step 2:
1-(benzenesulfonyl)-2-propyl-1H-pyrrolo[2,3-b]pyridine

To a stirred solution of 1-(benzenesulfonyl)-1H-pyrrolo[2,3-b]pyridine (400 mG, 1.55 mmol) in tetrahydrofuran (15 mL) at −78° C. was added n-BuLi (0.74 mL of a 2.5M solution in hexane, 1.86 mmol) dropwise. The mixture was stirred 1 h at −78° C. then warmed to rt for 5 min. The mixture was again cooled to −78° C. then iodo propane (0.45 mL, 4.65 mmol) was added and the mixture was stirred 1 h at rt. Water was added, and extractive workup (EtOAc) and purification (SiO$_2$, 20% EtOAc/hexane) gave 1-(benzenesulfonyl)-2-propyl-1H-pyrrolo[2,3-b]-pyridine.

Step 3: 2-propyl-1H-pyrrolo[2,3-b]pyridine

A mixture of 1-(benzenesulfonyl)-2-propyl-1H-pyrrolo[2,3-b]pyridine (67 mg) and KOH (200 mg) in MeOH (30 mL) was heated to reflux for 3 h. The mixture was concentrated, neutralized by addition of 1N HCl, extracted (EtOAc) and purified (SiO$_2$, 25% EtOAc/hexane) to give 2-propyl-1H-pyrrolo-[2,3-b]pyridine as a solid.

Step 4:
2-propyl-1-[[2'-(1-triphenylmethyl-1H-tetrazol-5-yl)[1,1']-biphenyl-4-yl]-methyl]-1H-pyrrolo[2,3-b]pyridine To a stirred mixture of 2-propyl-1H-pyrrolo-[2,3-b]pyridine (29 mg, 0.18 mmol) in DMF (1 mL) was added NaH (6.7 mg of an 80% dispersion in oil, 0.271 mmol). After 20 min, N-triphenylmethyl-5-(4'-bromomethylbiphen-2-yl)tetrazole (111 mg, 0.19 mmol) was added and the mixture was stirred for 30 min. Water was added and the mixture was extracted with EtOAc. Purification by flash chromatography (SiO$_2$, 25% EtOAc/hexanes) gave 2-propyl-1-[[2'-(1-triphenylmethyl-1H-tetrazol-5-yl)[1,1']-biphenyl-4-yl]methyl]-1H-pyrrolo[2,3-b]pyridine as a foam.

Step 5:
2-propyl-1-[[2'-(1H-tetrazol-5-yl)[1,1'-]-biphenyl-4-yl]methyl]-1H-pyrrolo[2,3-b]pyridine To a stirred solution of 4-methyl-2-propyl-1-[[2'-(1-triphenylmethyl-1H-tetrazol-5-yl)[1,1']-biphenyl-4-yl]methyl]-1H-pyrrolo[2,3-b]pyridine (68 mg, 0.11 mmol) in 30 mL of 2:1 MeOH—CH$_2$Cl$_2$ at rt was added 2 drops of conc HCl. After 30 min 3 drops of conc NH$_4$OH were added. Concentration and purification by flash chromatography (SiO$_2$, 25% EtOAc/hexanes) gave 2-propyl-1-[[2'-(1H-tetrazol-5-yl)-[1,1']-biphenyl-4-yl]methyl]-1H-pyrrolo[2,3-b]-pyridine as a solid. FAB MS M$^+$+1=395.

$^1$H NMR (CD$_3$OD, 400 MHz) δ8.11(1H, d, J=4 Hz), 7.90 (1H, d, J=7.8 Hz), 7.59 (2H, t, J=7.6 Hz), 7.48 (2H, t, J=7.6 Hz), 7.07 (1H, dd, J=4, 7.8 Hz), 7.00 (2H, d, J=7.9 Hz), 6.88 (2H, d, J=7.9 Hz), 6.33 (1H, s), 5.52 (2H, s), 2.63 (2H, t, J=7.8 Hz), 1.67 (2H, q, J=7.8 Hz), 0.97 (3H, t, J=7.8 Hz).

EXAMPLE 2

2-propyl-1-[(2'-carboxy-[1,1']-biphenyl-4-yl)methyl]-1H-pyrrolo[2,3-b]pyridine

Step 1:
2-propyl-1-[(2'-(t-butoxycarbonyl)-[1,1']-biphenyl-4-yl)methyl]-1H-pyrrolo[2,3-b]pyridine To a mixture of 2-propyl-1H-pyrrolo[2,3-b]-pyridine prepared in Example 1 step 3 (0.1M in DMF) is added NaH (1.1 equivalent of an 80% dispersion in oil, 0.271 mmol). After 20 min, 2-t-butoxycarbonyl-4'-bromomethylbiphenyl (1.1 equivalent) is added and the mixture is stirred for 30 min. Water is added and the mixture extracted with EtOAc. Purification by flash chromatography (SiO$_2$, 25% EtOAc/hexanes) gives 2-propyl-1-[(2'-t-butoxycarbonyl)-[1,1']-biphenyl-4-yl)methyl]-1H-pyrrolo[2,3-b]pyridine.

Step 2:
2-propyl-1-[(2'-carboxy-[1,1']-biphenyl-4-yl)methyl]-1H-pyrrolo[2,3-b]pyridine To neat 2-propyl-1-[(2'-(t-butoxycarbonyl)-[1,1']-biphenyl-4-yl)methyl]-1H-pyrrolo[2,3-b]pyridine is added trifluoroacetic acid (1 mL/10 mg of starting material) at room temperature. After 8 h the product is isolated by first concentration at room temperature then partitioning between EtOAc and 5% aqueous NaHCO$_3$ then concentration of the organic layer and ultimately purified by flash chromatography (80:20:1 CH$_2$Cl$_2$-MeOH—NH$_4$OH).

FORMULATION EXAMPLES

Typical Pharmaceutical Compositions Containing a Compound of the Invention

A: Dry Filled Capsules Containing 50 mg of Active Ingredient Per Capsule

| Ingredient | Amount per capsule (mg) |
| --- | --- |
| 2-propyl-1-(2'-(tetrazol-5-yl)biphen-4-yl)methyl-1H-pyrrolo[2,3-b]pyridine | 50 |
| Lactose | 149 |
| Magnesium stearate | 1 |
| Capsule (size No. 1) | 200 |

The 2-propyl-1-(2'-(tetrazol-5-yl)biphen-4-yl)methyl-1H-pyrrolo[2,3-b]pyridine can be reduced to a No. 60 powder and the lactose and magnesium stearate can then be passed through a No. 60 blotting cloth onto the powder. The combined ingredients can then be mixed for about 10 minutes and filled into a No. 1 dry gelatin capsule.

B: Tablet

A typical tablet would contain 2-propyl-1-(2'-(-tetrazol-5-yl)biphen-4-yl)methyl-1H-pyrrolo[2,3-b]pyridine(25 mg), pregelatinized starch USP (82 mg), microcrystalline cellulose (82 mg) and magnesium stearate (1 mg).

C: Combination Tablet

A typical combination tablet would contain, for example, a diuretic such as hydrochlorothiazide and consist of 2-propyl-1-(2'-(tetrazol-5-yl)-biphen-4-yl)methyl-1H-pyrrolo[2,3-b]pyridine (7.5 mg), hydrochlorothiazide (50 mg) pregelatinized starch USP (82 mg), microcrystalline cellulose (82 mg) and magnesium stearate (1 mg).

D: Suppository

Typical suppository formulations for rectal administration can contain 2-propyl-1-(2'-(tetrazol-5-yl)biphen-4-yl)methyl-1H-pyrrolo[2,3-b]pyridine (1-25 mg), butylated hydroxyanisole (0.08-1.0 mg), disodium calcium edetate (0.25-0.5 mg), and polyethylene glycol (775-1600 mg).

Other suppository formulations can be made by substituting, for example, butylated hydroxytoluene (0.04-0.08 mg) for the disodium calcium edetate and a hydrogenated vegetable oil (675-1400 mg) such as Suppocire L, Wecobee FS, Wecobee M, Witepsols, and the like, for the polyethylene glycol. Further, these suppository formulations can also include another active ingredient such as another antihypertensive and/or diuretic and/or an angiotensin converting enzyme and/or a calcium channel blocker in pharmaceutically effective amounts as described, for example, in C above.

E: Injection

A typical injectible formulation would contain 2-propyl-3-(2'-(tetrazol-5-yl)biphen-4-yl)methyl-1H-pyrrolo[2,3-b]pyridine (5.42 mg), sodium phosphate dibasic anhydrous (11.4 mg) benzyl alcohol (0.01 ml) and water for injection (1.0 ml). Such an injectible formulation can also include a pharmaceutically effective amount of another active ingredient such as another antihypertensive and/or a diuretic and/or an angiotensin converting enzyme inhibitor and/or a calcium channel blocker.

What is claimed is:

1. A compound of structural formula:

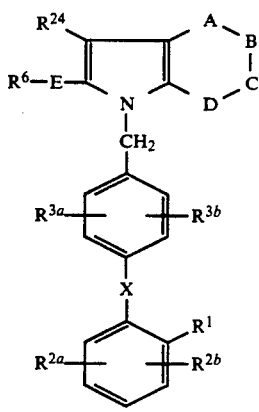

wherein:
$R^1$ is
(a) —$CO_2R^4$,
(b) —$SO_3R^5$,
(c) —$NHSO_2CF_3$,
(d) —$PO(OR^5)_2$,
(e) —$SO_2$—NH—$R^9$,
(f) —$CONHOR^5$,

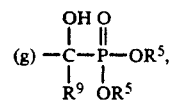

(g) —$SO_2NH$-heteroaryl,
(i) —$CH_2SO_2NH$-heteroaryl,
(j) —$SO_2NHCO$—$R^{23}$,
(k) —$CH_2SO_2NHCO$—$R^{23}$,
(l) —$CONH$—$SO_2R^{23}$,
(m) —$CH_2CONH$—$SO_2R^{23}$,
(n) —$NHSO_2NHCO$—$R^{23}$,
(o) —$NHCONHSO_2$—$R^{23}$,
(p) —$SO_2NHCONR^{23}$,

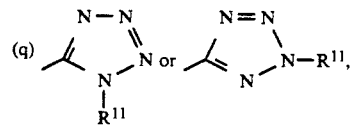

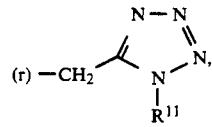

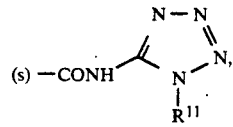

(t) —$CONHNHSO_2CF_3$,

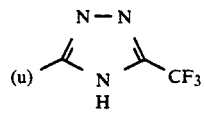

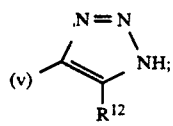

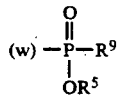

wherein heteroaryl is an unsubstituted, monosubstituted or disubstituted five- or six-membered aromatic ring which contains 1 to 3 heteroatoms selected from the group consisting of O, N or S and wherein the substituents are members selected from the group consisting of —OH, —SH, —$C_1$-$C_4$-alkyl, —$C_1$-$C_4$-alkoxy, Cl, Br, F, I, —$NO_2$, —CO$_2$H, —CO$_2$—C$_1$–C$_4$-alkyl, —NH$_2$, —NH(-C$_1$–C$_4$-alkyl) and —N(C$_1$–C$_4$-alkyl)$_2$;

R$^{2a}$ and R$^{2b}$ are independently H, Cl, Br, I, F, —NO$_2$, —NH$_2$, C$_1$–C$_4$-alkylamino, di(C$_1$–C$_4$ alkyl)amino, —SO$_2$NHR$^9$, CF$_3$, C$_1$–C$_4$-alkyl, or C$_1$–C$_4$-alkoxy;

R$^{3a}$ is
(a) H,
(b) Cl, Br, I, or F,
(c) C$_1$–C$_6$-alkyl,
(d) C$_1$–C$_6$-alkoxy, or
(e) C$_1$–C$_6$-alkoxyalkyl;

R$^{3b}$ is
(a) H,
(b) Cl, Br, I, or F,
(c) NO$_2$,
(d) C$_1$–C$_6$-alkyl,
(e) C$_1$–C$_6$-acyloxy,
(f) C$_1$–C$_6$-cycloalkyl,
(g) C$_1$–C$_6$-alkoxy,
(h) —NHSO$_2$R$^4$,
(i) hydroxy C$_1$–C$_4$-alkyl,
(j) aryl C$_1$–C$_4$-alkyl,
(k) C$_1$–C$_4$-alkylthio,
(l) C$_1$–C$_4$-alkylsulfinyl,
(m) C$_1$–C$_4$-alkylsulfonyl,
(n) NH$_2$,
(o) C$_1$–C$_4$-alkylamino,
(p) C$_1$–C$_4$-dialkylamino,
(q) fluoro C$_1$–C$_4$-alkyl,
(r) —SO$_2$—NHR$^9$,
(s) aryl, or
(t) furyl;
wherein aryl is phenyl or naphthyl or substituted phenyl or naphthyl with one or two substituents selected from the group consisting of Cl, Br, I, F, C$_1$–C$_4$-alkyl, C$_1$–C$_4$-alkoxy, NO$_2$, CF$_3$, C$_1$–C$_4$-alkylthio, OH, NH$_2$, NH(C$_1$–C$_4$-alkyl), N(C$_1$–C$_4$-alkyl)$_2$, CO$_2$H, and CO$_2$—C$_1$–C$_4$-alkyl;

R$^4$ is H, C$_1$–C$_6$ alkyl, aryl or —CH$_2$-aryl;
R$^{4a}$ is C$_1$–C$_6$-alkyl, aryl or —CH$_2$-aryl;
R$^5$ is

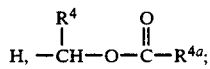

E is a single bond, —NR$^{13}$(CH$_2$)$_s$—, —S(O)$_x$—(CH$_2$)$_s$— where x is 0 to 2 and s is 0 to 5, —CH(OH)—, —O—, —CO—;

R$^6$ is
(a) aryl or substituted aryl with 1 or 2 substituents selected from the group consisting of Cl, Br, I, F —O—C$_1$–C$_4$-alkyl, C$_1$–C$_4$-alkyl, —NO$_2$, —CF$_3$, —SO$_2$NR$^9$R$^{10}$, —S—C$_1$–C$_4$-alkyl, —OH, —NH$_2$, C$_3$–C$_7$-cycloalkyl, C$_3$–C$_{10}$-alkenyl;
(b) C$_1$–C$_9$-alkyl, C$_2$–C$_6$-alkenyl or C$_2$–C$_6$-alkynyl or a substituted C$_1$–C$_9$ alkyl, C$_2$–C$_6$ alkenyl or C$_2$–C$_6$ alkynyl with a substituent selected from the group consisting of aryl, C$_3$–C$_7$-cycloalkyl, Cl, Br, I, F, —OH, —NH$_2$, —NH(C$_1$–C$_4$-alkyl), —CF$_2$CF$_3$, —N(C$_1$–C$_4$-alkyl)$_2$, —NH—SO$_2$R$^4$, —COOR$^4$, —CF$_3$, —CF$_2$CH$_3$, —SO$_2$NHR$^9$; or
(c) an unsubstituted, monosubstituted or disubstituted aromatic 5 or 6 membered cyclic ring which contains one or two members selected from the group consisting of N, O, S, and wherein the substituents are members selected from the group consisting of —OH, —SH, C$_1$–C$_4$-alkyl, C$_1$–C$_4$-alkyloxy —CF$_3$, Cl, Br, I, F, or NO$_2$,
(d) perfluoro-C$_1$–C$_4$-alkyl,
(e) C$_3$–C$_7$-cycloalkyl or mono- or disubstituted C$_3$–C$_7$-cycloalkyl with C$_1$–C$_4$-alkyl or —CF$_3$ substituent;

R$^9$ is H, C$_1$–C$_5$-alkyl, aryl or —CH$_2$-aryl;
R$^{10}$ is H, C$_1$–C$_4$-alkyl;
R$^{11}$ is H, C$_1$–C$_6$-alkyl, C$_2$–C$_4$-alkenyl, C$_1$–C$_4$-alkoxy-C$_1$–C$_4$-alkyl, or

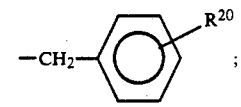

R$^{12}$ is —CN, —NO$_2$ or —CO$_2$R$^4$;
R$^{13}$ is H, —CO(C$_1$–C$_4$-alkyl), C$_1$–C$_6$-alkyl, allyl, C$_3$–C$_6$-cycloalkyl, phenyl or benzyl;
R$^{14}$ is H, C$_1$–C$_8$-alkyl, C$_1$–C$_8$-perfluoroalkyl, C$_3$–C$_6$-cycloalkyl, phenyl or benzyl;
R$^{15}$ is H, C$_1$–C$_6$-alkyl;
R$^{16}$ is H, C$_1$–C$_6$-alkyl, C$_3$–C$_6$-cycloalkyl, phenyl or benzyl;
R$^{17}$ is —NR$^9$R$^{10}$, —OR$^{10}$, —NHCONH$_2$, —NHCSNH$_2$,

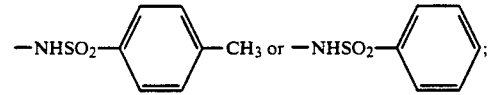

R$^{18}$ and R$^{19}$ are independently C$_1$–C$_4$-alkyl or taken together are —(CH$_2$)$_q$— where q is 2 or 3;
R$^{20}$ is H, —NO$_2$, —NH$_2$, —OH or —OCH$_3$;
R$^{23}$ is
(a) aryl,
(b) heteroaryl,
(c) C$_3$–C$_4$-cycloalkyl,
(d) C$_1$–C$_4$-alkyl or substituted C$_1$–C$_4$-alkyl with a substituent that is a member selected from the group consisting of aryl, heteroaryl, —OH, —SH, —C$_1$–C$_4$-alkyl, —O(C$_1$–C$_4$-alkyl), —S(-C$_1$–C$_4$-alkyl), —CF$_3$, Cl, Br, F, I, —NO$_2$, —CO$_2$H, —CO$_2$—C$_1$–C$_4$-alkyl, —NH$_2$, NH(C$_1$–C$_4$-alkyl), —NHCOR$^{4a}$, —N(C$_1$–C$_4$-alkyl)$_2$, —PO$_3$H, —PO(OH)(C$_1$–C$_4$-alkyl), —PO(OH)(aryl) or —PO(OH)(O—C$_1$–C$_4$-alkyl),
(e) perfluoro-C$_1$–C$_4$-alkyl;

R$^{24}$ is
(a) hydrogen,
(b) C$_1$–C$_6$ alkyl or substituted C$_1$–C$_6$ alkyl with a substituent selected from
(i) C$_1$–C$_4$ alkyloxy,
(ii) aryl,
(iii) —N(R$^4$)$_2$,
(iv) —OH,
(v) —CO$_2$R$^4$,
(vi) —CF$_3$,
(vii) —CON(R$^4$)$_2$, or
(viii) C$_3$–C$_7$ cycloalkyl,
(c) C$_3$–C$_7$ cycloalkyl or substituted C$_3$–C$_7$ cycloalkyl with a substituent selected from
(i) C$_1$–C$_4$ alkyl,
(ii) C$_1$–C$_4$ alkoxy,
(iii) aryl, (iv) —N(R⁴)₂,
(v) —OH,
(vi) —CO₂R⁴,
(vii) —CF₃, or
(viii) CON(R⁴)₂,
(d) aryl,
(e) —C₁-C₄ alkoxy,
(f) —C₁-C₄ acyloxy,
(g) —N(R⁸)CO₂R⁴ᵃ,
(h) —CN,
(i) —OC(O)OR⁴ᵃ,
(j) —OC(O)N(R⁴)₂,
(k) —N(R⁸)CON(R⁴)₂,
(l) —CF₃, —CF₂CF₃ or —CF₂CH₃,
(m) —OH or —SH, or
(n) —CO₂R⁴;

X is
(a) a carbon-carbon single bond,
(b) —CO—,
(c) —O—,
(d) —S—, (e) —N—,
     |
     R¹³

(f) —CON—,
     |
     R¹⁵

(g) —NCO—,
     |
     R¹⁵

(h) —OCH₂—,
(i) —CH₂O—
(j) —SCH₂—,
(k) —CH₂S—,
(l) —NHC(R⁹)(R¹⁰),
(m) —NR⁹SO₂—,
(n) —SO₂NR⁹—,
(o) —C(R⁹)(R¹⁰)NH—,
(p) —CH=CH—,
(q) —CF=CF—,
(r) —CH=CF—,
(s) —CF=CH—,
(t) —CH₂CH₂—,
(u) —CF₂CF₂—, (v) —CH——CH— and 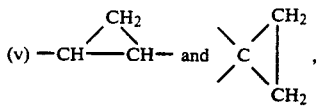,
        \\ //
         CH₂

(w) —CH—,
     |
     OR¹⁴

(x) —CH—
     |
     OCOR¹⁶

(y) —C— , or
     ||
     NR¹⁷

(z) —C— ;
     / \\
   R¹⁸O  OR¹⁹

Z is CH₂, O, NR¹³ or S;
—A—B—C—D— represents the constituent atoms of a 6-member saturated or unsaturated ring with the pyrrolo to which they are attached containing 1 nitrogen atom and includes the following:

1) 

2) 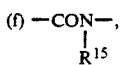

3) 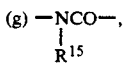

4)  R⁷   R⁷ R⁷
    |    |  |
    —C=N—C=C—,

5)  R⁷  R⁷ O  R⁸
    |   |  ||  |
    —C=C—C—N—,

6)  R⁷  R⁷ R⁸  O
    |   |  |   ||
    —C=C—N—C—,

7)  R⁸  O  R⁷ R⁷
    |   ||  |  |
    —N—C—C=C—,

8)  O   R⁸ R⁷ R⁷
    ||  |  |  |
    —C—N—C=C—,

9) 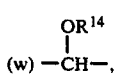

10) 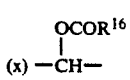

11) 

12) 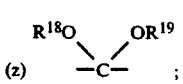

13)  O  R⁷ R⁷ R⁸
     ||  |  |  |
    —C—C=C—N—

14)  O  R⁹ᵃ      R⁹ᵃ R⁹ᵃ    R⁹ᵃ R⁸ᵃ
     || \\        \\   \\       \\  \\
    —C— C———————C————————C———N—,

15)  R⁹ᵃ      R⁹ᵃ R⁹ᵃ     R⁹ᵃ R⁸ R⁹ᵃ     R⁹ᵃ
     \\        \\   \\        \\  |  \\        \\
     —C———————C————————C—N————C—

R⁷ groups can be the same or different and represent:
a) hydrogen,
b) C₁-C₆ alkyl, or C₂-C₆ alkenyl, or alkynyl each of which is unsubstituted or substituted with:
   i) —OH
   ii) C₁-C₄-alkoxy,
   iii) —CO₂R⁴,
   iv) —OCOR⁴, v) 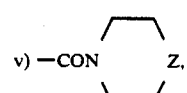

vi) —CON(R⁴)₂ vii) 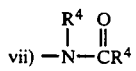

viii) —N(R⁴)₂,
ix) aryl,
x) heterocyclic as defined in (o) below,
xi) —S(O)ₓR²³,
xii) tetrazol-5-yl,
xiii) —CONHSO₂R²³,
xiv) —SO₂NH-heteroaryl,
xv) —SO₂NHCOR²³, xvi) 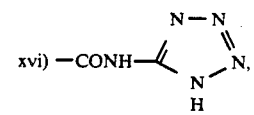

xvii) 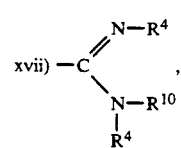

xviii) 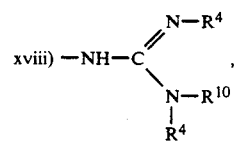

xix) —PO(OR⁴)₂,
xx) —PO(OR⁴)R⁹,
c) chloro, bromo or iodo,
d) perfluoro-C₁-C₄-alkyl,
e) —OH,
f) —NH₂, g) 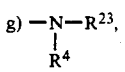

h) 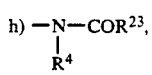

i) —OR²³,
j) —CO₂R⁴,
k) —CON(R⁴)₂,
l) —NH—C₃-C₇-cycloalkyl,
m) C₃-C₇ cycloalkyl,
n) aryl,
o) heterocyclic which is a five- or six-membered saturated or unsaturated ring containing up to three heteroatoms selected from the group consisting of O, N or S wherein S may in the form of sulfoxide or sulfone or a substituted heterocyclic with one or two substituents which are members selected from the group consisting of Cl, Br, F, I, C₁-C₄-alkyl, C₁-C₄-alkoxy, C₁-C₄—S(O)ₓ—, CF₃, NO₂, OH, CO₂H, CO₂—C₁-C₄-alkyl, NH₂, NH(C₁-C₄-alkyl) or N(R⁴)₂;
p) —CN, q) (CH₂)ₙ N— where n is 4 to 6, r) —SO₂N(R⁴)₂;
s) tetrazol-5-yl,
t) —CONHSO₂R²³,
u) —PO(OR⁴)₂,
v) —NHSO₂CF₃,
w) —SO₂NH-heteroaryl,
x) —SO₂NHCOR²³,
y) —S(O)ₓ—R²³, z) 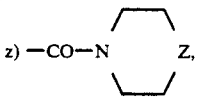

aa) —PO(OR⁴)R⁹,
bb) —NHSO₂R²³,
cc) —NHSO₂NHR²³,
dd) —NHSO₂NHCOR²³,
ee) NHCONHSO₂R²³,
ff) —N(R⁴)CO₂R²³, gg) 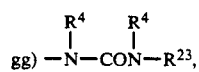

hh) —CO-aryl, ii) 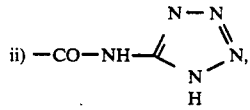

jj) —CO—C₁-C₄-alkyl,
kk) —SO₂NH—CN, ll) 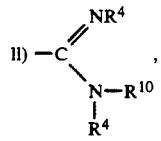

mm) 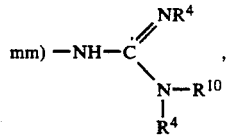

nn) 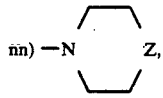

R⁸ groups can be the same or different and represent:
a) hydrogen,
b) C₁-C₆-alkyl or C₂-C₆ alkenyl either unsubstituted or substituted with aryl, hydroxy, C₁-C₄-alkoxy, —N(R⁴)₂, —CO₂R⁴ or C₃-C₅-cycloalkyl,
c) C₃-C₅-cycloalkyl;
R⁸ᵃ is R⁸ or C₁-C₄-acyl;

$R^{9a}$ groups can be the same or different and represent:
a) hydrogen,
b) $C_1$-$C_6$ alkyl either unsubstituted or substituted with
   i) hydroxy,
   ii) —$CO_2R^4$,
   iii) —$CONHR^4$, or
   iv) —$CON(R^4)_2$;
or, a pharmaceutically acceptable salt thereof.

2. The compound of claim 1, wherein:
$R^1$ is:
a) —$CO_2R^4$
b) —$NHSO_2CF_3$ c) [tetrazole structure with N—N, N, N, H]

d) —CONH—[tetrazole structure with N—N, N, N, H]

(e) —$SO_2NH$-heteroaryl,
(f) —$CH_2SO_2NH$-heteroaryl,
(g) —$SO_2NHCOR^{23}$,
(h) —$CH_2SO_2NHCOR^{23}$,
(i) —$CONHSO_2R^{23}$,
(j) —$CH_2CONHSO_2R^{23}$,
(k) —$NHSO_2NHCOR^{23}$,
(l) —$NHCONHSO_2R^{23}$, or
(m) —$SO_2NHCONHR^{23}$;

X is a single bond;

$R^{2a}$ and $R^{2b}$ are independently:
a) $C_1$-$C_4$-alkyl,
b) halogen, or
c) hydrogen;

$R^{3a}$ and $R^{3b}$ are independently:
a) $C_1$-$C_6$-alkyl,
b) halogen,
c) $C_1$-$C_6$-alkoxy, or
d) hydrogen;

$R^4$ is H, or $C_1$-$C_4$-alkyl;

E is a single bond or —S—;

$R^6$ is $C_1$-$C_6$-alkyl, $C_3$-$C_7$-cycloalkyl, $C_2$-$C_6$-alkenyl or $C_2$-$C_6$-alkynyl each of which is either unsubstituted or substituted with $C_1$-$C_4$-alkylthio, $C_1$-$C_4$-alkoxy, $CF_3$, —$CF_2CF_3$ or —$CF_2CH_2CH_3$;

and A—B—C—D— represents:

1) $-\overset{R^7}{\underset{|}{C}}=\overset{R^7}{\underset{|}{C}}-\overset{R^7}{\underset{|}{C}}=N-$, 2) $-\overset{R^7}{\underset{|}{C}}=\overset{R^7}{\underset{|}{C}}-N=\overset{R^7}{\underset{|}{C}}-$, 3) $-\overset{R^7}{\underset{|}{C}}=\overset{R^7}{\underset{|}{C}}-\overset{O}{\underset{||}{C}}-\overset{R^8}{\underset{|}{N}}-$, 4) $-\overset{R^7}{\underset{|}{C}}=\overset{R^7}{\underset{|}{C}}-\overset{R^8}{\underset{|}{N}}-\overset{O}{\underset{||}{C}}-$, -continued 5) $-\overset{R^{9a}}{\underset{\diagdown\diagup}{C}}\underset{}{-}\overset{R^{9a}\ R^{9a}}{\underset{\diagdown\diagup}{C}}\underset{}{-}\overset{R^{9a}\ R^{9a}}{\underset{\diagdown\diagup}{C}}\underset{}{-}\overset{R^{9a}\ R^{8a}}{\underset{\diagdown\diagup}{N}}-$.

6) $-\overset{R^{9a}}{\underset{\diagdown\diagup}{C}}\underset{}{-}\overset{R^{9a}\ R^{9a}}{\underset{\diagdown\diagup}{C}}\underset{}{-}\overset{R^{9a}\ O\ R^8}{\underset{\diagdown\diagup|}{C-N}}-$, 6) $-\overset{R^{9a}}{\underset{\diagdown\diagup}{C}}\underset{}{-}\overset{R^{9a}\ R^{9a}}{\underset{\diagdown\diagup}{C}}\underset{}{-}\overset{R^{9a}\ R^8\ O}{\underset{\diagdown\diagup|\ ||}{N-C}}-$;

$R^7$ groups are the same or different and represent:
a) hydrogen,
b) —$C_1$-$C_4$-alkyl, either unsubstituted or substituted with:
   i) OH,
   ii) —$CO_2R^4$,
   iii) —$NH_2$,
   iv) ($C_1$-$C_4$-alkyl)amino,
   v) di($C_1$-$C_4$ alkyl)amino,
c) halo,
d) —$CF_3$,
e) —OH,
f) —$N(R^4)_2$,
g) —$C_1$-$C_4$-alkoxy,
h) —$CO_2R^4$,
i) —$CONH_2$,
j) —$C_3$-$C_7$-cycloalkyl,
k) aryl,
l) heterocyclic,
m) —$CF_3$,
n) tetrazol-5-yl,
o) —$CONHSO_2R^{23}$;

$R^8$ groups are the same or different and represent,
a) hydrogen,
b) $C_1$-$C_4$-alkyl either unsubstituted or substituted with —OH or —$CO_2R^4$;

$R^{8a}$ represents
a) hydrogen,
b) $C_1$-$C_4$ alkyl, or
c) ($C_1$-$C_4$-alkyl)CO—;

$R^{9a}$ groups are the same or different and represent:
a) hydrogen,
b) $C_1$-$C_4$-alkyl; and $R^{24}$ is
a) hydrogen,
b) $C_1$-$C_6$ alkyl,
c) $C_3$-$C_7$ cycloalkyl,
d) cyclopropylmethyl,
e) —$CF_3$, or
f) —OH.

3. The compound of claim 2 wherein:
$R^1$ is
a) —$CO_2R^4$ b) [tetrazole structure with N—N, N, N, H]

c) —$NHSO_2CF_3$,
d) —$SO_2NH$—heteroaryl,
e) —$CH_2SO_2NH$—heteroaryl,
f) —$SO_2NHCOR^{23}$,
g) —$CH_2SO_2NHCOR^{23}$,
h) —$CONHSO_2R^{23}$, or i) —CH$_2$CONHSO$_2$R$^{23}$;

E is a single bond; and,

A—B—C—D represents:

1) 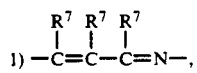

2) 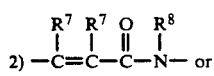 or

4. A compound according to claim 1 of the formula (II):

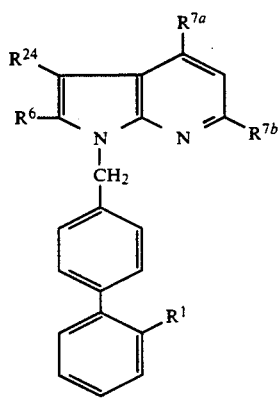

wherein:

R$^1$ is
 (a) —CO$_2$R$^4$,
 (b) —NH$^2$SO$_2$CF$_3$, (c) 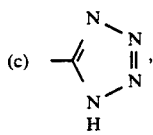

(d) —CONHSO$_2$Ph,
 (e) —CONHSO$_2$Ph—2—Br,
 (f) —SO$_2$NHCOPh, or
 (g) —SO$_2$NHCO cyclopropyl;

R$^4$ is hydrogen or C$_1$-C$_4$ alkyl;

R$^6$ is C$_1$-C$_6$ alkyl, C$_2$-C$_6$ alkenyl or C$_3$-C$_7$ cycloalkyl;

R$^{7a}$ and R$^{7b}$ independently are
 (a) hydrogen,
 (b) C$_1$-C$_4$ alkyl,
 (c) substituted C$_1$-C$_4$ alkyl in which the substituent is
  (i) hydroxy,
  (ii) —CO$_2$R$^4$
  (iii) amino,
  (iv) C$_1$-C$_4$ alkylamino,
  (v) di(C$_1$-C$_4$ alkyl)amino, or
 (d) C$_1$-C$_4$ alkoxy; and R$^{24}$ is hydrogen, C$_1$-C$_6$ alkyl or C$_3$-C$_7$ cycloalkyl.

5. A compound of claim 4 wherein:

R$^1$ is
 (a) —CO$_2$R$^4$, or (b) 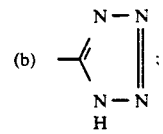

R$^4$ is hydrogen or C$_1$-C$_4$ alkyl;

R$^6$ is C$_1$-C$_6$ alkyl, or C$_3$-C$_7$ cycloalkyl;

R$^{7a}$ and R$^{7b}$ independently are
 (a) hydrogen,
 (b) C$_1$-C$_6$ alkyl, or
 (c) —CO$_2$R$^4$; and R$^{24}$ is hydrogen or C$_1$-C$_6$ alkyl.

6. A compound of claim 5 which is 2-propyl-1-[[2'-(1H-tetrazol-5-yl)[1,1'-biphenyl-4-yl]methyl]-1H-pyrrolo[2,3-b]pyridine.

7. A compound of claim 5 which is 2-propyl-1-[(2'-carboxy-[1,1']-biphenyl-4-yl)methyl]-1H-pyrrolo[2,3-b]pyridine.

8. A compound of claim 1 of the formula

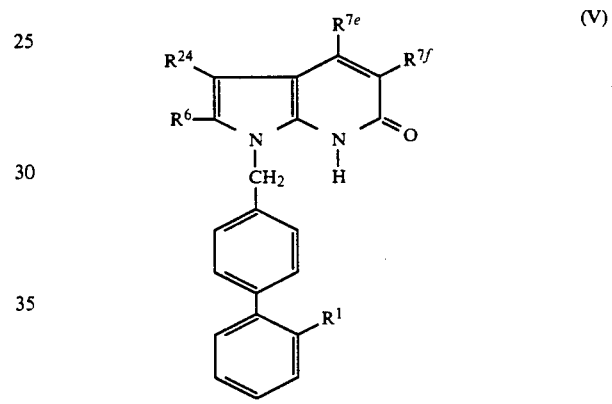

wherein:

R$^1$ is
 (a) —CO$_2$R$^4$, (b) 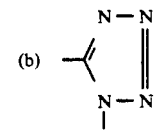, (c) —SO$_2$NHCOPh, or
 (d) —SO$_2$NHCO cyclopropyl;

R$^4$ is hydrogen or C$_1$-C$_4$ alkyl;

R$^6$ is C$_1$-C$_6$ alkyl, C$_2$-C$_6$ alkyl or C$_3$-C$_7$ cycloalkyl;

R$^{7e}$ and R$^{7f}$ independently are
 (a) hydrogen,
 (b) C$_1$-C$_4$ alkyl, or
 (c) substituted alkyl in which the substituent is
  (i) hydroxy,
  (ii) —CO$_2$R$^4$,
  (iii) amino,
  (iv) C$_1$-C$_4$ alkylamino,
  (v) di(C$_1$-C$_4$ alkyl)amino, or
  (vi) alkoxy; and R$^{24}$ is hydrogen or C$_1$-C$_6$ alkyl.

9. A pharmaceutical formulation for the treatment of hypertension and congestive heart failure comprising a pharmaceutically acceptable carrier and an effective antihypertensive amount of the compound of claim 1.

10. A method of treating hypertension and congestive heart failure comprising the administration of an effective antihypertensive amount of the compound of claim 1 to a patient in need of such treatment.

11. An ophthalmological formulation for the treatment of ocular hypertension comprising an ophthalmologically acceptable carrier and an effective ocular antihypertensive amount of a compound of claim 1.

12. A method of treating ocular hypertension comprising administering to a patient in need of such treatment an effective ocular antihypertensive amount of a compound of claim 1.

* * * * *